Figure 1:
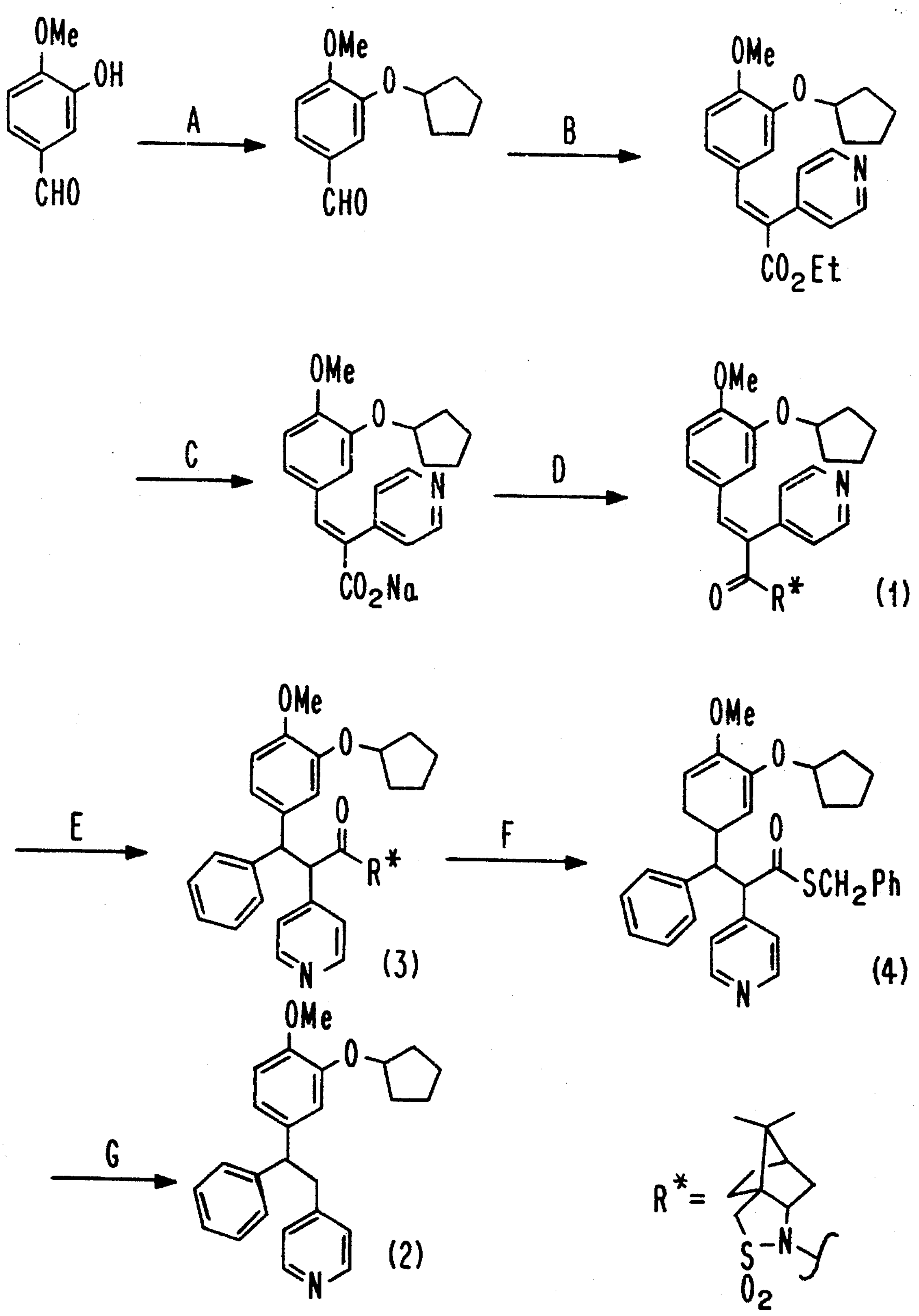

US005608070A

United States Patent [19]

Alexander et al.

[11] Patent Number: 5,608,070

[45] Date of Patent: Mar. 4, 1997

[54] ENANTIOSELECTIVE PROCESS FOR THE PREPARATION OF CHIRAL TRIARYL DERIVATIVES AND CHIRAL INTERMEDIATES FOR USE THEREIN

[75] Inventors: Rikki P. Alexander, High Wycombe; Graham J. Warrellow, Northwood; John C. Head, Windsor; Ewan C. Boyd, Tullibody; John R. Porter, Chinnor, all of United Kingdom

[73] Assignee: Celltech Therapeutics Limited, Slough, United Kingdom

[21] Appl. No.: 361,439

[22] Filed: Dec. 21, 1994

[30] Foreign Application Priority Data

Dec. 22, 1993 [GB] United Kingdom .................. 9326173

[51] Int. Cl.$^6$ .................................................. C07D 417/00

[52] U.S. Cl. .......................... 546/270; 544/333; 548/123; 548/208; 548/341.5

[58] Field of Search ............................ 544/333; 548/123, 548/208, 241.5; 546/340, 270, 271.1

[56] References Cited

U.S. PATENT DOCUMENTS

| | | | |
|---|---|---|---|
| 4,012,495 | 3/1977 | Schmiechen et al. | 424/274 |
| 4,015,017 | 3/1977 | Gazave | 424/331 |
| 4,153,713 | 5/1979 | Huth et al. | 424/274 |
| 4,193,926 | 3/1980 | Schmiechen et al. | 260/326.5 |
| 4,303,649 | 12/1981 | Jones | 424/177 |
| 4,792,561 | 12/1988 | Walker et al. | 514/312 |
| 4,921,862 | 5/1990 | Walker et al. | 514/312 |
| 4,971,959 | 11/1990 | Hawkins | 514/150 |
| 5,124,455 | 6/1992 | Lombardo | 546/181 |
| 5,128,358 | 7/1992 | Saccomano et al. | 514/392 |
| 5,175,167 | 12/1992 | Zipperer et al. | 514/277 |
| 5,177,085 | 1/1993 | Naef | 514/307 |
| 5,236,918 | 8/1993 | Amschler et al. | 514/247 |
| 5,274,002 | 12/1993 | Hawkins | 514/530 |
| 5,298,511 | 3/1994 | Waterson | 514/311 |
| 5,326,898 | 7/1994 | Chandraratna | 560/17 |

FOREIGN PATENT DOCUMENTS

| | | |
|---|---|---|
| 0393500 | 10/1990 | European Pat. Off. . |
| 0490823 | 6/1991 | European Pat. Off. . |
| 0470805 | 2/1992 | European Pat. Off. . |
| 0497564 | 8/1992 | European Pat. Off. . |
| 0511865 | 11/1992 | European Pat. Off. . |
| 0537742 | 4/1993 | European Pat. Off. . |
| 2501443 | 7/1975 | Germany . |
| 1588639 | 4/1981 | United Kingdom . |
| WO87/06576 | 11/1987 | WIPO . |
| WO91/15451 | 10/1991 | WIPO . |
| WO91/16892 | 11/1991 | WIPO . |
| WO92/00968 | 1/1992 | WIPO . |
| WO92/06963 | 4/1992 | WIPO . |
| WO92/06085 | 4/1992 | WIPO . |
| WO92/07567 | 5/1992 | WIPO . |
| WO92/12961 | 8/1992 | WIPO . |
| WO92/19602 | 11/1992 | WIPO . |
| WO92/19594 | 11/1992 | WIPO . |
| WO93/19748 | 10/1993 | WIPO . |
| WO94/02465 | 2/1994 | WIPO . |
| WO94/12461 | 6/1994 | WIPO . |
| WO94/14742 | 7/1994 | WIPO . |

OTHER PUBLICATIONS

Ashton, "Selective Type IV Phosphodiesterase Inhibitors as Antiasthmatic Agents. The Syntheses and Biological Activities of 3–(Cyclopentyloxy)–4–methyoxybenzamides and Analogues" J. Med. Chem. 37: 1696–1703 (1994).

Beavo & Reifsnyder, "Primary Sequence of Cyclic Nucleotide Phosphodiesterase Isozymes and the Design of Selective Inhibitors" TIPS 11: 150–155 (1990).

Buu–Hoi, N.P. et al., "Bromination of Some 1,2,2–Triarylethylenes" *J. of Organic Chemistry*, 1261–1263 (Sep., 1958).

Buu–Hoi et al., "New Method for the Synthesis of ω,ω–Diarylacetophenones Aminated in the Aromatic Nucleus. Plynitration of Triarylethylenes" Chemical Abstracts 61: 16006h (1964).

Chemical Abstracts. Registry Handbook—Number Section. Printed Issues Columbus US *compounds with registry numbers 95992–21–5; 95971–60–1; 90053–37–5; 82668–18–6; 80395–25–1; 49610–49–3.

El–Wakil et al., "Study of the proton magnetic resonance of methoxytamoxifen towards ortho–substitution" Chemical Abstacts 116: 255248t (1992).

Hirose et al., "Styrene Derivatives and Electrophotpgraphic Photoreceptor Containing Them" Chemical Abstracts 118: 136183z (1993).

Lisle, H. et al., "IL–2–Induced Eosinophilia in the Rat Pleural Cavity: The Effect of Dexamethasone and Indomethacin", *Br. J. Pharmacol.* 1993, 108, 230.

(List continued on next page.)

*Primary Examiner*—Amelia Owens

*Attorney, Agent, or Firm*—Woodcock Washburn Kurtz Mackiewicz & Norris

[57] ABSTRACT

An enantioselective multi-stage process is described which uses as a starting material an α,β-unsaturated olefin of formula (1):

$$Ar—CH=C(R^4)COAux \quad (1)$$

where Ar and $R^4$, which may be the same or different, is each a monocyclic or bicyclic aryl group optionally containing one or more heteroatoms selected from oxygen, sulphur or nitrogen atoms; and Aux is the residue of a chiral (R- or S-) auxiliary.

In the process, the olefin is converted to a chiral triarylethane which is of use in medicine.

16 Claims, 1 Drawing Sheet

OTHER PUBLICATIONS

Livi et al., "Cloning and Expression of cDNA for a Human Low–$K_m$3 Rolipram–sensitive Cyclic AMP Phosphodiesterase", *Molecular and Cellular Biol.* 1990, 10, 2768.

Ishikura, M. et al., "An Efficient Synthesis of 3–Heteroarylpyridines via Diethyl–(3–pyridyl)–borane" Synthesis pp. 936–938 (1984).

Manhas et al., "Heterocyclic Compounds XII. Quinazoline Derivatives as Potential Antifertility Agents (1)" J. Heterocyclic Chem: 711–715 (1979).

Meyers, A. J. et al., "Oxazolines. XI. Synthesis of Functionalized Aromatic and Aliphatic Acids. A Useful Protecting Group for Carboxylic Acids Against Grignard and Hydride Reagents", *J. Org. Chem.* 1974, 39, 2787.

Mezheritskaya, "Synthesis and properties of carboxonium heterocyclic systems. VII. Synthesis and properties of 2–benzyl–substituted 1,3–dioxolanium salts" Chem. Abs. 93: 95160j p. 635 (1980).

Mitsunobu, O., "The Use of Diethyl Azodicarboxylate and Triphenylphosphine in Synthesis and Transformation of Natural Products" Synthesis 1–28 (1981).

Nicholson et al., "Differential Modulation of Tissue Function and Therapeutic Potential of Selective Inhibitors of Cyclic Nucleotide Phosphodiesterase Isoenzymes" TIPS 12: 19–27 (1991).

O'Connor et al., "Voltammetry and Controlled Potential Oxidation of 3,4–dimethoxypropenylbenzene at a rotating platinum electrode in unbuffered acetonitrile and in acetonitrile–pyridine solution" Chemical Abstracts 60 (8) #10203.4 (Apr. 13, 1964).

Porter et al., "Preparation of 6–phenyl–3–(5–tetrazolyl)pyridin=2(H)–one Derivatives as Cyclic AMP–dependent Protein Kinase Agonists" Chem. Abstract 117 (9): 90296n (1992).

Ramalingam, Deshmukh and Sattur, "Synthesis and Pharmacology of 2,5–Disubstituted 1,3,4–Zxadiazoles" J. Indian Chem. Soc. vol. 58 (3) 269–271 (1981).

Reddy et al., "Inhibition of Breast Cancer Cell Growth in Vitro by a Tyrosine Kinase Inhibitor" Cancer Research 52: 3636–3641 (1992).

Schneider et al., "Catechol Estrogens of the 1,1, 2–Triphenylbut–1–ene Type: Relatoinship Between Structure, Estradiol Receptor Affinity, Estrogenic and Antiestrogenic Properties and Mammary Tumor Inhibiting Activities" J. Med. Chem. 29: 1355–1362 (1986).

Seitz et al., "Fluorotamoxifen. A Caveat on the Generality of Electrophilic Destannylation" Chemical Abstracts 111: 57136k (1989).

Sharp, M. J. et al., "Synthetic Connections to the Aromatic Directed Metalation Reaction. Functionalized Aryl Boronic Acids by Ipso Borodesilylation; General Synthesis of Unsymmetrical iphenyls and n–Terphenyls" Tetrahedron Lett 28: 5093–5096 (1987).

Thompson, W.J. and Gaudino, J., "A General Synthesis of 5–Arylnicotinates" J. Org. Chem. 49: 5237–5243 (1984).

Yeadon et al., "Mechanisms Contributing to Ozone–Induced Bronchial Hyperreactivity in Guinea Pigs", *Pulmonary Pharm.* 1992, 5, 39.

Yoneda et al., "The Antiproliferative Effects of Tyrosine Kinase Inhibitors Tyrphostins on a Human Squamous Cell Carcinoma in Vitro and in Nude Mice" Cancer Research 51: 4430–4435 (1991).

Mathison, I. et al., "Synthesis and Hypotensive Properties of Tetrahydroisoquinolines", *J. of Medicinal Chemistry* 1973, 16(4), 332–336.

Sakakibara, K. et al., "Preparation of N–pyridyl–4–(benzyloxy)benzamides as Cardiotonics", Chem. Abstr. 1988, vol. 108, No. 131583p.

Takeuchi, I. et al., "On the antimocrobial Activity and Syntheses of Carbanilide and Salicylanilide Derivatives", *Chem. Abstr.* 1983, 98, No. 125577y.

ENANTIOSELECTIVE PROCESS FOR THE PREPARATION OF CHIRAL TRIARYL DERIVATIVES AND CHIRAL INTERMEDIATES FOR USE THEREIN

This invention relates to an enantioselective process for the preparation of chiral triarylethanes and to novel chiral intermediates for use therein.

In our European Patent Specification No. 626939 we describe the triarylethane (±)-4-[1-(3-cyclopentyloxy-4-methoxyphenyl)-2-phenylethyl]pyridine. The compound has the formula:

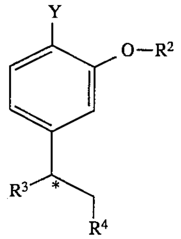

[where Y is methoxy, —O—$R^2$ is cyclopentyloxy, —$R^3$ is phenyl, and —$R^4$ is 4-pyridyl] and by virtue of an asymmetric carbon atom [identified in the formula above by the asterisk] can exist as a R- or S-isomer. Each isomer is an orally active, potent selective inhibitor of the isoenzyme phosphodiesterase IV [PDE IV]. This enzyme plays a major role in the hydrolysis of adenosine 3',5'-cyclic monophosphate [cAMP] in inflammatory leukocytes and airway smooth muscle. It can be expected therefore that each isomer, as a selective inhibitor of PDE IV, would have therapeutic effects in inflammatory diseases such as asthma, by achieving both anti-inflammatory and bronchodilator effects.

Although each of the R- or S-isomers may be isolated from a corresponding mixture, for example either via the preparation of diastereomeric derivatives or by chiral High Performance Liquid Chromatography, this approach is not very satisfactory, particularly on an industrial scale, where it is difficult to produce material of acceptable enantiomeric purity for clinical use, in good yield. In order to overcome this problem, we have developed an enantioselective process, making use of novel chiral intermediates, the operation of which is capable of giving directly each of the isomers in high yield with an e.e. (enantiomeric excess) value of at least 98%. The process is particularly robust and may be extended generally to the large scale manufacture of chiral triarylethanes of 95% e.e. or greater.

A key compound in the enantioselective process is an α,β-unsaturated olefin of formula (1):

$$Ar—CH{=}C(R^4)COAux \qquad (1)$$

[where Ar and $R^4$, which may be the same or different, is each a monocyclic or bicyclic aryl group optionally containing one or more heteroatoms selected from oxygen, sulphur or nitrogen atoms; and Aux is the residue of a chiral (R- or S-) auxiliary] which forms a first aspect of the present invention.

The olefins of formula (1) are the starting materials for an enantioselective process which yields an R- or S-isomer of formula (2):

$$Ar—\underset{\underset{R^3}{\wr}}{C}HCH_2R^4 \qquad (2)$$

where Ar and $R^4$ are as defined for formula (1), $R^3$ is a monocyclic or bicyclic aryl group optionally containing one or more heteroatoms selected from oxygen, sulphur or nitrogen atoms, said $R^3$ group being either the same as or different to the groups Ar and $R^4$, and where the wavy line (~) means that the configuration at —CH($R^3$)— is either the R- or S-configuration.

According to a further aspect of the invention, we provide an olefin of formula (1) for use in an enantioselective process for the preparation of a R- or S-isomer of formula (2). R- or S-isomers of formula (2), particularly those more specifically described hereinafter, have utility as pharmacological agents for use in medicine, for example as selective PDE IV inhibitors for use in the prophylaxis or treatment of inflammatory diseases such as asthma.

Particular examples of olefins according to the invention are given in the Examples, including the Tables, and FIG. 1 hereinafter. FIG. 1, in particular, provides a reaction scheme which illustrates the overall enantioselective process to a particular isomer of formula (2). In general terms, however, we provide in a further aspect of the invention, a multistage process for the preparation of a R- or S-isomer of formula (2), which comprises, in a first step reacting a compound of formula (1) with an $R^3$-containing organometallic reagent to yield a compound of formula (3):

$$Ar—\underset{\underset{R^3}{\wr}}{C}HCH(R^4)COAux \qquad (3)$$

where Ar, $R^3$, $R^4$ and Aux are as defined previously; followed, in a second step, by cleavage of the compound of formula (3) with a thiol [RSH] in the presence of a base to yield a thioester of formula (4):

$$Ar—\underset{\underset{R^3}{\wr}}{C}HCH(R^4)COSR \qquad (4)$$

[where —SR is the residue of a thiol and R is an organic group] and followed in a final step by decarbonylation of the intermediate of formula (4) to yield the desired R- or S-isomer of formula (2).

The intermediates of formulae (3) and (4) above are novel, useful compounds and form a further aspect of the invention.

It will be appreciated that the compounds of formula (1) can form geometric as well as chiral isomers, and the invention is intended to cover all possible such isomers of the compounds. The particular isomer selected for use in the process according to the invention will determine the nature of the isomer of formula (2) obtained as a result. Thus, for example, in FIG. 1 a process is illustrated in which the Ar [3-cyclopentyloxy-4-methoxyphenyl] and $R^4$ [4-pyridyl] groups in the compound of formula (1) are in a cis (E) relationship. In this example, when the chiral auxiliary ($R^*$ in the figure) is a R-isomer the resulting compound of formula (2) is a R-isomer. Alternatively in the same example, but with the use of a compound of formula (1) in which the Ar and $R^4$ groups are in a trans (Z) relationship, the corresponding S-isomer of formula (2) is generated. Other stereochemical combinations of Ar, $R^4$ and Aux will be readily apparent from this, and the particular relationship can be initially selected, depending on the nature of Ar, $R^4$ and Aux, to achieve the optimum process for the particular, desired isomer of formula (2).

In the first step of the multi-stage process according to the invention, the $R^3$-containing organometallic reagent may be for example a Grignard reagent $R^3MgHal$ [where Hal is a halogen atom such as a bromine atom] or an organolithium compound $R^3Li$. When a Grignard reagent is used, the reaction is preferably carried out in the presence of a complexing agent, e.g. a copper (I) bromide-dimethyl sulphide complex or copper (I) chloride. The reaction may be performed in an inert solvent, for example an acyclic or cyclic ether e.g. diethylether or tetrahydrofuran at a low temperature, e.g. around −70° C. to around 0° C. Any necessary subsequent quenching may be carried out using an electrophile, for example a hydrogen donor such as aqueous ammonium chloride, at a low temperature, such as −30° C. to −20° C.

In the second step of the process, the thiol may be for example a reagent RSH where R is an organic group such as an alkyl group, e.g. a $C_{1-4}$alkyl group such as an ethyl or propyl group, or an aralkyl group, e.g. a $C_{6-12}$ar$C_{1-3}$alkyl group such as a benzyl group. The base may be an organometallic base, for example an organolithium base such as an alkyllithium, e.g. n-butyllithium base. The reaction may be performed in an inert solvent, e.g. an ether such as a cyclic ether, e.g. tetrahydrofuran at a low temperature, e.g. around 0° C. to around ambient temperature, such as 0° C. to 25° C.

In the final step of the process, the decarbonylation of the intermediate of formula (4) may be achieved by heating the compound in the presence of a base followed by acidification to a pH in the range around pH4 to around pH6 at an elevated temperature e.g. the reflux temperature. The base may be for example an inorganic base such as a hydroxide, e.g. sodium or potassium hydroxide in a solvent such as an alcohol e.g. ethanol. Once the reaction with base is complete the mixture may be acidified to the desired pH, using for example an inorganic acid such as hydrochloric acid and heated to yield the desired isomer of formula (2).

In this part of the process, the thioester intermediate of formula (4) is initially transformed to the corresponding carboxylic acid where —SR is replaced by —OH. The carboxylic acid spontaneously decarboxylates to the desired R- or S-isomer either at room temprature or by heating up to the reflux temperature, particularly when the group $R^4$ is an electron deficient group such as a 2-pyridyl or 4-pyridyl group. Where spontaneous decarboxylation does not occur it may be necessary to isolate the carboxylic acid and heat strongly to the melt temperature, or to chemically decarboxylate, for example by converting the acid to the corresponding aldehyde and then treating the aldehyde with a catalyst, for example Wilkinson's catalyst $[RhCl(Ph_3P)_3]$ or $Rh(CO)(PPh_3)_2Cl$ [where Ph is phenyl] in the presence of 1,3-bis(diphenylphosphino)propane in an inert solvent such as toluene at an elevated temperature e.g. around 100° C. The aldehyde may be generated from the acid by any convenient means, for example by reduction of the acid to the corresponding alcohol, using for example a hydride such as lithium aluminium hydride or sodium borohydride followed by oxidation of the alcohol to the aldehyde using an oxidising agent such as pyridinium chlorochromate, pyridinium dichlorochromate or Jones reagent.

If desired, the multi-stage process according to the invention may be operated without the isolation of the thioester intermediate of formula (4).

In the above process steps, the progress end completion of any particular reaction may be followed by the use of any appropriate analytical technique, for example by the use of NMR or by analytical chromatography such as by thin layer chromatography.

The process according to the invention is particularly effective when $R^4$ in the starting materials of formula (1) is an electron-withdrawing group. Particular electron-withdrawing groups include 5- or 6-membered nitrogen containing heteroaryl groups, such as imidazolyl, or pyridyl, particularly 2- or 4-pyridyl groups.

In the starting materials of formula (1), the residue of the chiral auxiliary, Aux, may be for example the residue of a cyclic or acyclic sultam, alcohol, or amine containing one ore more homochiral centres. Particular sultams include for example R- or S-10,2-bornanesultam. Particular alcohols include for example those derived from menthol, e.g. R- or S-8-phenylmenthol, or camphor. Particular amines include oxazolines, e.g. oxazolidinones, ephedrines and prolinols. In general the group Aux is preferably the residue of a R- or S-sultam, particularly R- or S-10,2-bornanesultam.

Particularly useful compounds of formula (1) include:

(E)-N-[3-(3-Cyclopentyloxy-4-methoxyphenyl)-2-(4-pyridyl)propenoyl]-(1R)-10,2-bornanesultam; or (Z)-N-[3-(3-Cyclopentyloxy-4-methoxyphenyl)-2-(4-pyridyl)propenoyl]-(1R)-10,2-bornanesultam; or (E)-N-[3-(3-Cyclopentyloxy-4-methoxyphenyl)-2-(4-pyridyl)propenoyl]-(1S)-10,2-bornanesultam; or (Z)-N-[3-(3-Cyclopentyloxy-4-methoxyphenyl)-2-(4-pyridyl)propenoyl]-(1S)-10,2-bornanesultam; or (E)-N-3-Phenyl-2-(4-pyridyl)propenoyl-(1R)-10,2-bornanesultam; or (Z)-N-3-Phenyl-2-(4-pyridyl)propenoyl-(1R)-10,2-bornanesultam; or (E)-N-3-Phenyl-2-(4-pyridyl)propenoyl-(1S)-10,2-bornanesultam; or (Z)-N-3-Phenyl-2-(4-pyridyl)propenoyl-(1S)-10,2-bornanesultam.

The starting materials of formula (1) may be prepared by reaction of an active derivative of an acid of formula (5):

$$Ar—CH=C(R^4)CO_2H \quad (5)$$

for example an acid halide such as the acid chloride with either the R- or S- chiral auxiliary (Aux-H) as appropriate, in the presence of a base, such as sodium hydride in a solvent, e.g. tetrahydrofuran or dichloromethane.

The active derivative of the acid of formula (6) may be prepared from the corresponding acid using conventional procedures. For example, where the acid chloride is desired this may be obtained by reacting the acid with thionyl chloride or oxalyl chloride in a solvent such as dichloromethane at a temperature from around 0° C. to around the reflux temprature.

The chiral auxiliaries for use in this reaction are commercially available compounds [from e.g. the Aldrich Chemical Co.], or may be prepared from known compounds using methods analogous to those used for the preparation of the commercially available compounds.

The acid of formula (5) may be prepared by reaction of an aldehyde of formula (6):

$$Ar—CHO \quad (6)$$

with an ester $R^4CH_2CO_2CH_2CH_3$ in a solvent such as toluene in the presence of an acid such as acetic acid or benzoic acid and a base such as piperidine, at an elevated temperature such as the reflux temperature, followed by saponification of the resulting ester using an inorganic base such as sodium hydroxide in a solvent such as tetrahydrofuran at an elevated temperature such as the reflux temperature.

The aldehydes of formula (6) are either known compounds [see for example European Patent Specification No.

626939] or may be prepared by methods analogous to those used for the preparation of the known compounds.

In the following pages, the groups Ar, $R^3$ and $R^4$ in compounds of formulae (1), (2), (3) and (4) are described more fully.

Thus, monocyclic or bicyclic aryl groups represented by the groups Ar, $R^3$ or $R^4$ include for example $C_{6-12}$ optionally substituted aryl groups, for example optionally substituted phenyl, 1- or 2-naphthyl, indenyl or isoindenyl groups.

When the monocyclic or bicyclic aryl group Ar, $R^3$ or $R^4$ contains one or more heteroatoms it may be for example a $C_{1-9}$ optionally substituted heteroaryl group containing for example one, two, three or four heteroatoms selected from oxygen, sulphur or nitrogen atoms. In general, the heteroaryl groups may be for example monocyclic or bicyclic heteroaryl groups. Monocyclic heteroaryl groups include for example five- or six-membered heteroaryl groups containing one, two, three or four heteroatoms selected from oxygen sulphur or nitrogen atoms.

Examples of heteroaryl groups represented by Ar, $R^3$ or $R^4$ include pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, isobenzothienyl, indolyl, isoindolyl, benzimidazolyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetra-hydroquinolinyl and 5,6,7,8-tetrahydroisoquinolinyl.

The heteroaryl group represented by Ar, $R^3$ or $R^4$ may be attached to the remainder of the molecule through any ring carbon or heteroatom as appropriate. Thus, for example, when the group Ar, $R^3$ or $R^4$ is a pyridyl group it may be a 2-pyridyl, 3-pyridyl or 4-pyridyl group. When it is a thienyl group it may be a 2-thienyl or 3-thienyl group, and, similarly, when it is a furyl group it may be a 2-furyl or 3-furyl group.

The aryl or heteroaryl groups represented by Ar, $R^3$ or $R^4$ may each optionally be substituted by one, two, three or more substituents [$R^5$]. The substituent $R^5$ may be selected from an atom or group $R^5$ or $-Alk^1(R^6)_m$ wherein $R^6$ is a halogen atom, or an amino ($-NH_2$), substituted amino, nitro, cyano, hydroxyl (—OH), substituted hydroxyl, cycloalkoxy, formyl [HC(O)—], carboxyl ($-CO_2H$), esterified carboxyl, thiol (—SH), substituted thiol, $-C(O)Alk^1$, $-SO_3H$, $-SO_2Alk^1$, $-SO_2NH_2$, $-SO_2NHAlk^1$, $-SO_2N[Alk^1]_2$, $-CONH_2$, $-CONHAlk^1$, $-CON[Alk^1]_2$, $-NHSO_2H$, $-NHSO_2Alk^1$, $-N[SO_2Alk^1]_2$, $-NHSO_2NH_2$, $-NHSO_2NHAlk^1$, $-NHSO_2N[Alk^1]_2$, $-NHC(O)Alk^1$, or $-NHC(O)OAlk^1$ group; $Alk^1$ is a straight or branched $C_{1-6}$alkylene. $C_{2-6}$alkenylene, or $C_{2-6}$alkynylene chain optionally interrupted by one, two, or three —O—, or —S— atoms or —S(O)p—, [where p is an integer 1 or 2] or $-N(R^8)-$ groups; and m is zero or an integer 1, 2 or 3.

When in the group $-Alk^1(R^6)_m$ m is an integer 1, 2 or 3, it is to be understood that the substituent or substituents $R^6$ may be present on any suitable carbon atom in $-Alk^1$. Where more than one $R^6$ substitutent is present these may be the same or different and may be present on the same or different carbon atom in $Alk^1$. Clearly, when m is zero and no substituent $R^6$ is present or when $Alk^1$ forms part of a group such as $-SO_2Alk^1$ the alkylene, alkenylene or alkynylene chain represented by $Alk^1$ becomes an alkyl, alkenyl or alkynyl group.

When $R^6$ is a substituted amino group it may be a group $-NH[Alk^1(R^{6a})_m]$ [where $Alk^1$ and m are as defined above and $R^{13a}$ is as defined above for $R^6$ but is not a substituted amino, a substituted hydroxyl or a substituted thiol group] or a group $-N[Alk^1(R^{6a})_m]_2$ wherein each $-Alk^1(R^{13a}a)_m$ group is the same or different.

When $R^6$ is a halogen atom it may be for example a fluorine, chlorine, bromine, or iodine atom.

When $R^6$ is a cycloalkoxy group it may be for example a $C_{5-7}$cycloalkoxy group such as a cyclopentyloxy or cyclohexyloxy group.

When $R^6$ is a substituted hydroxyl or substituted thiol group it may be a group $-OAlk^1(R^{6a})_m$ or $-SAlk^1(R^{6a})_m$ respectively, where $Alk^1$, $R^{6a}$ and m are as just defined.

Esterified carboxyl groups represented by the group $R^6$ include groups of formula $-CO_2Alk^2$ wherein $Alk^2$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxymethyl, 1-naphthyloxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the $Alk^2$ group include $R^5$ substituents described above.

When $Alk^1$ is present in or as a substituent $R^5$ it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, $-S(O)_2-$ or $-N(R^7)-$ groups where $R^7$ is a hydrogen atom or a $C_{1-6}$alkyl group such as a methyl or ethyl group.

Particularly useful atoms or groups represented by $R^5$ include fluorine, chlorine, bromine or iodine atoms, or $C_{1-6}$alkyl, e.g. methyl or ethyl, $C_{1-6}$alkylamino, e.g. methylamino or ethylamino, $C_{1-6}$ hydroxyalkyl, e.g. hydroxymethyl or hydroxyethyl, $C_{1-6}$alkylthiol e.g. methylthiol or ethylthiol, $C_{1-6}$alkoxy, e.g. methoxy or ethoxy, $C_{5-7}$cyclcoalkoxy, e.g. cyclo-pentyloxy, halo$C_{1-6}$alkyl, e.g. trifluoromethyl, $C_{1-6}$alkylamino, e.g. methylamino or ethylamino, amino ($-NH_2$), amino$C_{1-6}$alkyl, e.g. aminomethyl or aminoethyl, $C_{1-6}$dialkylamino, e.g. dimethylamino or diethylamino, nitro, cyano, hydroxyl (—OH), formyl [HC(O)—], carboxyl ($-CO_2H$), $-CO_2Alk^2$ [where $Alk^2$ is as defined above], $C_{1-6}$ alkanoyl e.g. acetyl, thiol (—SH), thio$C_{1-6}$alkyl, e.g. thiomethyl or thioethyl, sulphonyl ($-SO_3H$), $C_{1-6}$alkylsulphonyl, e.g. methylsulphonyl, aminosulphonyl ($-SO_2NH_2$), $C_{1-6}$alkylaminosulphonyl, e.g. methylaminosulphonyl or ethylaminosulphonyl, $C_{1-6}$dialkylaminosulphonyl, e.g. di-methylaminosulphonyl or diethylaminosulphonyl, carboxamido ($-CONH_2$), $C_{1-6}$alkylaminocarbonyl, e.g. methylamino-carbonyl or ethylaminocarbonyl, $C_{1-6}$dialkylaminocarbonyl, e.g. dimethylaminocarbonyl or diethylaminocarbonyl, sulphonylamino ($-NHSO_2H$), $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, aminosulphonylamino ($-NHSO_2NH_2$), $C_{1-6}$alkylaminosulphonylamino, e.g.

methylaminosulphonylamino or ethylaminosulphonylamino, $C_{1-6}$dialkylaminosulphonylamino, e.g. dimethylaminosulphonylamino or diethylaminosulphonylamino, $C_{1-6}$alkanoylamino, e.g. acetylamino, $C_{1-6}$alkanoylamino $C_{1-6}$alkyl, e.g. acetylaminomethyl or $C_{1-6}$alkoxycarbonylamino, e.g. methoxycarbonylamino, ethoxycarbonylamino or t-butoxycarbonylamino groups.

Where desired, two $R^5$ substituents may be linked together to form a cyclic group such as a cyclic ether, e.g. a $C_{2-6}$alkylenedioxy group such as ethylenedioxy.

It will be appreciated that where two or more $R^5$ substituents are present, these need not necessarily be the same atoms and/or groups. The $R^5$ substituents may be present at any ring carbon atom away from that attached to the rest of the molecule of formula (3). Thus, for example, in phenyl groups represented by Ar any substituent may be present at the 2-, 3-, 4-, 5- or 6-positions relative to the ring carbon atom attached to the remainder of the molecule.

The above compounds and process according to the invention may in particular be used to prepare R- or S-isomers of formula (2) which have the general formula (2a):

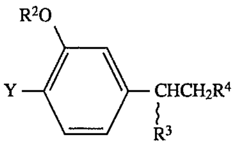

(2a)

where

Y is a halogen atom or a group —$OR^1$ where $R^1$ is an optionally substituted alkyl group;

$R^2$ is an optionally substituted alkyl, alkenyl, cycloalkyl or cycloalkenyl group;

$R^3$ and $R^4$, which may be the same or different, is each a monocyclic or bicyclic aryl group optionally containing one or more heteroatoms selected from oxygen, sulphur or nitrogen atoms;

and the wavy line (~) means that the configuration at —$CH(R^3)$— is either the R- or S-configuration.

In the compounds of formula (3), when Y is a halogen atom it may be for example a fluorine, chlorine, bromine or iodine atom.

When Y in the compounds of formula (3) is a group —$OR^1$, $R^1$ may be, for example, an optionally substituted straight or branched alkyl group, for example, an optionally substituted $C_{1-6}$alkyl group, such as a methyl, ethyl, n-propyl or i-propyl group. Optional substitutents which may be present on $R^1$ groups include one or more halogen atoms, e.g. fluorine, or chlorine atoms. Particular substituted alkyl groups include for example —$CH_2F$, —$CH_2Cl$, —$CHF_2$, —$CHCl_2$, —$CF_3$ or —$CCl_3$ groups.

Alkyl groups represented by $R^2$ in the compounds of formula (3) include optionally substitutes straight or branched $C_{1-6}$ alkyl groups, e.g. $C_{1-3}$ alkyl groups such as methyl or ethyl groups. Optional substituents on these groups include one, two or three substituents selected from halogen atoms, e.g. fluorine, chlorine, bromine or iodine atoms, or hydroxyl or $C_{1-6}$ alkoxy e.g. $C_{1-3}$ alkoxy such as methoxy or ethoxy groups.

Alkenyl groups represented by $R^2$ in the compounds of formula (3) include optionally substituted straight or branched $C_{2-6}$alkenyl groups such as ethenyl, propen-1-yl and 2-methylpropen-1-yl. Optional substituents include those described above in relation to the groups $R^2$.

When $R^2$ in the compounds of formula (3) is an optionally substituted cycloalkyl or cycloalkenyl group it may be for example a $C_{3-8}$cycloalkyl group such as a cyclobutyl, cyclopentyl or cyclohexyl group or a $C_{3-8}$ cycloalkenyl group containing for example one or two double bonds such as a 2-cyclobuten-1-yl, 2-cyclopenten-1-yl, 3-cyclopenten-1-yl, 2,4-cyctopentadien-1-yl, 2-cyclohexen-1-yl, 3-cyclohexen-1-yl, 2,4-cyclohexadien-1-yl or 3,5-cyclohexadien-1-yl group, each cycloalkyl or cycloalkenyl group being optionally substituted by one, two or three substituents selected from halogen atoms, e.g. fluorine, chlorine, bromine or iodine atoms, straight or branched $C_{1-6}$alkyl e.g. $C_{1-3}$alkyl such as methyl or ethyl, hydroxyl or $C_{1-6}$alkoxy e.g. $C_{1-3}$alkoxy such as methoxy or ethoxy groups.

In the compounds of formula (2a) the group Y is preferably an —$OR^1$ group, especially where $R^1$ is an optionally substituted ethyl group or, especially, an optionally substituted methyl group. Especially useful substitutents which may be present on $R^1$ groups include one, two or three fluorine or chlorine atoms.

$R^2$ is preferably an optionally substituted methyl or cyclopentyl group. In particular, $R^2$ is a cyclopentyl group.

Particularly useful $R^3$ or $R^4$ groups in the compounds of formula (2a) include monocyclic aryl groups optionally containing one or more heteroatoms selected from oxygen, sulphur, or, in particular, nitrogen atoms, and optionally substituted by one, two, three or more $R^5$ substituents. In these compounds, when the group represented by Ar, $R^3$ or $R^4$ is a heteroaryl group it is preferably a nitrogen-containing monocyclic heteroaryl group, especially a six-membered nitrogen-containing heteroaryl group. Thus, in one preferred example, the groups $R^3$ and $R^4$ may each be a six-membered nitrogen-containing heteroaryl group. In another preferred example $R^3$ may be a monocyclic aryl group or monocyclic heteroaryl group containing an oxygen or sulphur atom and $R^4$ may be a six-membered nitrogen-containing heteroaryl group. In these examples, the six-membered nitrogen-containing heteroaryl group may be an optionally substituted pyridyl, pyridazinyl, pyrimidinyl or pyrazinyl group. Particular examples include optionally substituted 2-pyridyl, 3-pyridyl or, especially, 4-pyridyl, 3-pyridazinyl, 4-pyridazinyl, 5-pyridazinyl, 2-pyrimidinyl, 4-pyrimidinyl, 5-pyrimidinyl, 2-pyrazinyl or 3-pyrazinyl. The monocyclic aryl group may be a phenyl group or a substituted phenyl group, and the monocyclic heteroaryl group containing an oxygen or sulphur atom may be an optionally substituted 2-furyl, 3-furyl, 2-thienyl or 3-thienyl group.

One particularly useful group of compounds of formula (2a) is that wherein $R^3$ and $R^4$ is each a pyridyl or, especially, a monosubstituted pyridyl, or preferably a disubstituted pyridyl group, or $R^3$ is a phenyl, thienyl or furyl, or substituted phenyl, thienyl or furyl group and $R^4$ is a pyridyl or, especially a monosubstituted pyridyl, or preferably a disubstituted pyridyl group.

In this particular group of compounds, when $R^3$ and/or $R^4$ is a substituted phenyl group it may be for example a mono-, di- or trisubstituted phenyl group in which the substituent is an atom or group $R^5$ as defined above. When the $R^3$ and/or $R^4$ group is a monosubstituted phenyl group the substituent may be in the 2-, or preferably 3-, or especially 4-position relative to the ring carbon atom attached to the remainder of the molecule.

When in compounds of formula (2a) $R^4$ and/or $R^4$ is a substituted pyridyl group it may be for example a mono-or disubstituted pyridyl group, such as a mono- or disubstituted 2-pyridyl, 3-pyridyl or especially 4-pyridyl group substituted by one or two atoms or groups $R^5$ as defined above, in particular one or two halogen atoms such as fluorine or chlorine atoms, or methyl, methoxy, hydroxyl or nitro groups. Particularly useful pyridyl groups of these types are 3-monosubstituted-4-pyridyl or 3,5-disubstituted-4-pyridyl, or 2- or 4-monosubstituted-3-pyridyl or 2,4-disubstituted-3-pyridyl groups.

The compounds and process according to the invention are particularly useful for preparing:

(R)-(+)-4-[2-(3-Cyclopentyloxy-4-methoxyphenyl)-2-phenylethyl]pyridine;

(S)-(−)-4-[2-(3-Cyclopentyloxy-4-methoxyphenyl)-2-phenylethyl]pyridine;

(R)-(+)-4-[1-(3-Cyclopentyloxy-4-methoxyphenyl)-2-(4-pyridyl)ethyl]pyridine; or (S)-(−)-4-[1-(3-Cyclopentyloxy-4-methoxyphenyl)-2-(4-pyridyl)ethyl]pyridine.

The presence of certain substituents in the compounds of formula (2) may enable salts of the compounds to be formed. The last step in the enantioselective process may therefore be salt formation and the process of the invention is intended to extend to this. Salts may be formed by reaction of the R- or S-isomer of formula (3) with an appropriate acid or base in a suitable solvent e.g. an organic solvent suich as an ether, using conventional procedures. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds of formula (2) include pharmaceutically acceptable salts, especially acid addition pharmaceutically acceptable salts.

The following Examples and Tables illustrate the process and compounds according to the invention. In Example 1, reference is made to FIG. 1, which illustrates the individual steps and intermediates in the process. All NMR data was obtained in $CDCl_3$ unless otherwise stated.

EXAMPLE 1

In this Example, Steps E, F and G illustrate the process according to the invention, and the compound of Step D part (ii) is a compound according to the invention.

STEP (A)

3-Cyclopentyloxy-4-methoxybenzaldehyde (Step A of FIG. 1)

To a stirred solution of 3-hydroxy-4-methoxybenzaldehyde (140 g; 0.92 mol) in dimethylformamide (700 ml) was added dry potassium carbonate (2.54 g; 1.84 mol). The mixture was neared to 55° C. and cyclopentyl bromide (74 g; 1.97 ml; 1.84 mol) in dimethylformamide (300 ml) was added dropwise over 2 hours. After complete addition, the mixture was stirred at 55° C. for 15 hours, cooled, filtered and the solvent removed in vacuo. The residue was dissolved in $CH_2Cl_2$ and washed with 1.0M NaOH to eliminate any trace of phenol. The organic layer was dried ($MgSO_4$) and purified by column chromatography ($SiO_2$; $CH_2Cl_2$). The solution was concentrated in vacuo to give the title compound as an oil (192 g). $\delta_H$ ($CDCl_3$) 1.5–2.0 (8H, br m, $(CH_2)_4$), 3,87 (3H, s, O<u>Me</u>), 4.80 (1H, br m, OC<u>H</u>$CH_2$), 6.90 (1H, d, <u>J</u> 8.7 Hz, Ar<u>H ortho</u> to O<u>Me</u>), 7.30–7.45 (2H, m, 2×Ar<u>H meta</u> to O<u>Me</u>) and 9.77 (1H. s, ArC<u>H</u>O)

STEP (B)

Ethyl 3-(3-Cyclopentyloxy-4-methoxyphenyl)-2-(4-pyridyl) Propenoate (Step B of FIG. 1)

A mixture of the aldehyde of Step A (26.62 g; 0.12 mol), ethyl-4-pyridyl-acetate (19.92 g; 0.12 mol; 1 eq) and ammonium acetate (18.63 g; 0.24 g; 2 eq) in glacial acetic acid (200 ml) was stirred at 120° C. under $N_2$ for 20 hours. The solution was cooled to room temperature and the acid removed in vacuo to give an orangey/brown residue. This residue was taken up in a saturated bicarbonate solution (to pH=8.5) and extracted several times with ethyl acetate. The combined organic layer was washed with brine, dried ($MgSO_4$) and evaporated to dryness to give a yellow solid. Recrystallisation from toluene/hexane (1st crop) then toluene (2nd crop) followed by column chromatography ($SiO_2$; hexane-EtOAc/hexane: 7/3) gave the title compound m.p. 109°–111° C. as a white crystalline solid. $\delta_H$ ($CDCl_3$) 1.27 (3H, t, <u>J</u> 7.1 Hz, $CH_2C\underline{H}_3$), 1.45–1.8 (8H, br m, cyclopentyl <u>H</u>'s), 3.81 (3H, s, O<u>Me</u>), 4.16 (1H, br m, OC<u>H</u>), 4.25 (2H, q, <u>J</u> 7.1 Hz, $C\underline{H}_2CH_3$), 6.43 (1H, d, <u>J0</u> 2.0 Hz, Ar<u>H ortho</u> to cyclopentylolxy), 6.73 (1H, d, <u>J</u> 8.4 Hz, Ar<u>H</u> ortho to O <u>Me</u>), 6.80 (1H, dd, <u>J</u> 2.0, 8.4 Hz, Ar<u>H</u> para to cyclopentyloxy), 7.22 (2H, dd, <u>J</u> 1.6, 4.5 Hz, pyridine $\underline{H}_3$, $\underline{H}_5$), 7.83 (1H, s, <u>H</u>C=C) and 8.64 (2H, dd, <u>J</u> 1.6, 4.5 Hz, pyridine $\underline{H}_2$, $\underline{H}_6$).

An alternative procedure is as follows:

To a stirred solution of the aldehyde of Step A (22 g; 100 mmol and ethyl-4-pyridyl-acetate (16.5 g; 100 mmol) in dry toluene (150 ml) at room temperature was added glacial acetic acid (2.4 ml) followed by piperidine (0.8 ml). The solution was heated to reflux and the water produced removed as an azeotrope, collected by a Dean Stark Apparatus. After 16 hrs, the solution was allowed to cool to room temperature, charcoal and Florisil added, stirred for 5 minutes and then filtered. The solvent was removed by evaporation in vacuo. The crystalline solid obtained was dissolved in dichloromethane, washed with a saturated sodium bicarbonate solution, dried ($MgSO_4$), filtered and the solvent removed by evaporation in vacuo. The product was recrystallised (diisopropyl ether) to give the title compound as a white crystalline solid, with melting point and NMR consistent with the above values.

STEP (C)

(E)-3-(3-Cyclopentyloxy-4-methoxyphenyl)-2-(4-pyridyl)propenoic Acid Hydrochloride (Step C of FIG. 1)

To a stirred solution of the ester of Step B (36.89 g; 100.5 mmol) in tetrahydrofuran (300 ml) was added an aqueous (300 ml) sodium hydroxide (6.03 g; 150 mmol; 1.5 eq) solution. The reaction mixture was heated at reflux for 3 hours, cooled to room temperature, then acidified to pH 1–1.5 by slow addition of concentrated hydrochloric acid (27 ml). The solvent was removed in vacuo to give the title compound as a pale yellow solid. $\delta_H$ ($CDCl_3$) 1.5–1.85 (8H, br m, cyclopentyl <u>H</u>'s), 3.81 (3H, s, O<u>Me</u>), 4.44 (1H, br m, OC<u>H</u>), 6.55 (2H, m, 2×Ar<u>H meta</u> to O<u>Me</u>), 6.79 (1H, d, <u>J</u> 8.3

Hz, ArHortho to OMe), 7.81 (2H, d, J 6.0 Hz, pyridine $H_3$, $H_5$), 8.07 (1H, s, HC=C) and 8.81 (2H, d, J 6.0 Hz, pyridine $H_2$, $H_6$).

N.B: The compound contains 1.5 eq sodium chloride.

(i) (E)-3-(3-Cyclopentyloxy-4-methoxyphenyl)-2-(4-pyridyl)propenoyl Chloride Hydrochloride To a stirred suspension of the acid of Step (C) (5.52 g; 11.9 mmol) (containing 1.5 eq NaCl) in dichloromethane (60 ml) was added neat thionyl chloride. The reaction mixture was heated under gentle reflux for 45 min or until completion of reaction as determined by cessation of HCl gas evolution or by $^1$Hnmr (in $CDCl_3$) of an aliquot. The solvent and excess thionyl chloride were removed in vacuo, with several azeotropes with dry toluene and dichlorethane, to give the title compound as a dirty yellow powdery solid; $\delta_H$ ($CDCl_3$) 1.5–1.7 (2H, br m, cyclopentyl H'S), 1.7–1.9 (6H, br m, cyclopentyl H's), 3.87 (3H, s, OMe), 4.5 (1H, br m, OCH, 6.61 (2H, m, 2×ArH meta to OMe), 6.76 (1H, d, J 8.8 Hz, ArH ortho to OMe), 7.88 (2H, d, J 6.0 Hz, pyridine $H_3$, $H_5$), 8.35 (1H, s, HC=C) and 8.92 (2H, d, J6.0 Hz, pyridine $H_2$, $H_6$).

(ii) (E)-N[3-(3-Cyclopentyloxy-4-methoxyphenyl)-2-(4-pyridyl)propenoyl]-(1R)-10,2-bornanesultam The acid chloride of part (i) (5.86 g; 12.2 mmol) was added to a cold (–40° C.) solution of sultam salt R*Na [generated from (2S)-Bornane-10,2-sultam (2.48 g; 11.6 mmol; 0.95 eq) and sodium hydride (60% disp in oil) (1.95 g; 48.7 mol; 4 eq.) in tetrahydrofuran (120 ml) under $N_2$ at room temperature and stirred for 30 mins)]. After 30 mins, dichloromethane (20 ml) was added and the reaction mixture stirred at –20° C. for a further 30 mins. The reaction was quenched with 10% ammonium chloride solution (20 ml) and tetrahydrofuran removed in vacuo. The residue was partitioned between half saturated sodium bicarbonate solution (150 ml) and ethyl acetate (150 ml). The aqueous phase was re-extracted with ethyl acetate (2×50 ml), the combined organic layer washed with brine (30 ml), dried ($MgSO_4$) and evaporated in vacuo to give an orange glassy solid. Flash chromatography ($SiO_2$; 50% ethyl acetate/hexane) afforded the title compound as a pale yellow foamy solid. $\delta_H$ ($CDCl_3$) 1.01 (3H, s, CMe), 1.14 (3H, s, CMe), 1.3–2.2 (15H, br m, 8×cyclopentyl H's+7×sultam H's), 3.43 (1H, d, J 13.7 Hz, $HCHSO_2$), 3.55 (1H, d, J 13.7 Hz, $HCHSO_2$, 3.80 (3H, s, O Me), 4.07 (1H, t, J 6.2 Hz, NCH),4.19 (1H, br, m, OCH), 6.47 (1H, d, J 2.0 Hz, ArHortho to cyclopentyl), 6.73 (1H, d, J 8.2 Hz, ArH ortho to OMe), 6.82 (1H, dd. J 2.0 Hz, 8.2 Hz, ArH para to cyclopentyloxy), 7.33 (1H, s, HC=C), 7.36 (2H, dd, J 1.4, 4.4 Hz, pyridine $H_3$, $H_5$) and 8.59 (2H, dd, J 1.4, 4.4 Hz, pyridine $H_2$, $H_6$).

STEP (E)

N-[(3R)-3-(3-Cyclopentyloxy-4-methoxyphenyl)-3-phenyl-2-(4-pyridyl) Propanoyl]-(1R)-10,2-bornanesultam (Step E of FIG. 1)

To a stirred solution of the acyl sultam of Step D (28.15 g; 56.2 mmol) in tetrahydrofuran/ether (5:1; 180 ml) at –70° C. under $N_2$ was added phenylmagnesium bromide (3M in ether) (41.4 ml; 123.6 mmol; 2.2 eq) dropwise. The mixture was allowed to warm to –40° C. (±20° C.) and stirred at this temperature for 1.25 hr. The solution was quenched with a 10% aqueous ammonium chloride solution (40 ml) and partitioned between ethyl acetate (500 ml) and water (500 ml) and the aqueous layer extracted several times with ethyl acetate. The combined organic layer was washed with brine (100 ml), dried ($MgSO_4$) and the solvent removed in vacuo give a yellow solid which was recrystallised from ethanol (500 ml) to afford the title compound as white needles. $\delta_H$ ($CDCl_3$) 0.75 (3H, s, CMe), 0.88 (3H, s, CMe), 1.1–2.0 (15H, br m, 8×cyclopentyl H's+7×sultam H's), 3,31 (1H, d, J 13.8 Hz, $HCHSO_2$), 3.45 (1H, d, J 13.8 Hz, $HCHSO_2$), 3.68 (3H, s, OMe), 3.7–3.75 (1H, m, NCH), 4.55 (1H, d, J 11.5 Hz, PhCHCH), 4.57 (1H, br m, OCH), 5.06 (1H, d, J 11.5 Hz, PhCHCH), 6.55–6.65 (3H, m, ArH), 7.1–7.2 (1H, m, ArH), 7.2–7.3 (2H, m, ArH) 7.33 (2H, dd, J 1.6, 4.5 Hz, pyridine $H_3$, $H_5$), 7.47 (2H, d, J 7.2 Hz, ArH) and 8.39 (2H, dd, J 1.6, 4.5 Hz, pyridine $H_2$, $H_6$).

STEP (F)

(R)-3-(3-Cyclopentyloxy-4-methoxyphenyl)-3-phenyl-2-(4-pyridyl) Ethane Carboxythioethane (Step F of FIG. 1)

To a solution of ethanethiol (0.99 g; 13.4 mmol; 2.6 eq) in tetrahydrofuran (30 ml) at 0° C. under $N_2$ was added n-Butyllithium (1.6M in hexane) (4.82 ml; 7.71 mmol; 1.5 eq). The white slurry was stirred at 0° C. for 15 mins and a solution of the acyl sultam of Step E (3.16 g; 5.1 mmol; 1 eq) in tetrahydrofuran (40 ml) was added. The reaction mixture was left to warm to room temperature and stirred for 3 hrs. The solution was concentrated to dryness in vacuo and the residue obtained used in the final step.

STEP (G)

(R)-(+)-4-[2-(3-Cyclopentyloxy-4-methoxyphenyl)-2-phenylethyl]pyridine (Step G of FIG. 1)

A stirred solution of the crude compound of Step (F) in aqueous NaOH solution (2M; 100 ml) and ethanol (50 ml) was heated to reflux for 1 hr. At 50°–65° C., the pH was adjusted to pH 6–6.65 with concentrated hydrochloric acid solution, and the reaction mixture heated under gentle reflux for 10–15 min. The reaction was made alkaline with aqueous NaOH before being concentrated in vacuo. The oily residue was partitioned between ether (100 ml) and water (100 ml), the aqueous layer was re-extracted with ether (2×100 ml), the combined organic layer washed with 1M aqueous NaOH (40 ml) and water (40 ml) and then extracted with 10% aqueous HCl (2×50 ml). The combined acid extract was extracted with ether (2×30 ml) and made basic by adding solid NaOH. The oil produced was extracted into ether (2×75 ml) and the extract washed with brine (30 ml), dried ($MgSO_4$) and evaporated to give a near colourless oil. Purification by column chromatography ($SiO_2$; $Et_2O$/Hexane: 70/30→$Et_2O$) gives the title compound as a colourless glass. $\delta_H$ ($CDCl_3$) 1.5–2.1 (8H, br m $(CH_2)_4$), 3.27 (2H, d, J 8.0 Hz, $CH_2$ pyridine), 3.75 (3H, s, OMe), 4.12 (1H, t, J 8.0 Hz, $PhCHCH_2$), 4.61 (1H, br m, $OCHCH_2$), 6.5–6.7 (3H, m, ArH ortho to OMe+2×ArH meta to OMe), 6.87 (2H, dm, J 4.5 Hz, pyridine $H_3$, $H_5$), 7.05–7.2 (5H, m, $C_6H_5$), and 8.32 (2H, dm, J 4.5 Hz, pyridine $H_2$, $H_6$).

EXAMPLES 2–18

Steps (E), (F) and (G) of Example 1 (the process according to the invention) were repeated to yield the compounds (Compound Nos. 1–17) shown in Tables 1, 2, 4 and 5. In each instance, the acyl sultam prepared as in Step D of Example 1 was reacted with the appropriate $R^3$ containing Grignard reagent to yield the compounds 1–17 shown in Tables 1 and 2. The resulting acyl sultams were then treated as described in Steps (F) and (G) to yield the final product isomers (1–17) described in Tables 4 and 5.

EXAMPLE 19

This Example illustrates the preparation of the compound 20 (Tables 4 and Steps (F) and (G) below describe the process according to the invention. Step (E) describes the preparation of a compound according to the invention.

To a stirred solution of 3-thiophene carboxaldehyde (20 g, 178 mmol) and ethyl-4-pyridylacetate (29.4 g, 178 mmol) in dry toluene (250 ml) at room temperature and under a nitrogen atmosphere, was added glacial acetic acid (4.2 ml) and piperidine (1.4 ml). The mixture was stirred under reflux, with a Dean & Stark trap fitted, for 18 h, the toluene was evaporated in vacuo and the resulting solid recrystallised from ethanol to give, after washing with the same solvent (at 0° C.) an off-white solid. The filtrate was evaporated and the residue subjected to flash column chromatography ($SiO_2$; EtOAc/hexane, 1:1) to give a further portion of the product. The two crops were combined and recrystallised from ethanol to give (E)-ethyl-3-(3-thiophene)-2-(4-pyridyl-)propenate as a white crystalline solid (26.83 g, 58%) p.m. 104°–106° C.

A solution of the ester (26.0 g, 100.4 mmol) in tetrahydrofuran (200 ml) was treated with potassium hydroxide (11.3 g, 200 mmol) in water (200 ml), and stirred under reflux for 2 h. The mixture was cooled to room temperature and the tetrahydrofuran evaporated in vacuo; the residue was adjusted to pH 5.5 with concentrated HCl and the precipitated white solid collected by filtration and dried in a vacuum over at 90° C. to give (E)-3-(3-thiophene)-2-(4-pyridyl)propenoic acid hydrochlorine (22.86 g, 98.6%) m.p. 212°–213° C. dec.

STEP (E)

To a suspension of sodium hydride (60% disp, 4.16 g, 104 mmol) in dry tetrahydrofuran (800 ml) at room temperature, and under a nitrogen atmosphere, was added, in portions, the acid. This was stirred for 40 m (thick white ppt of sodium carboxylate formed) and then phosphorus oxychloride (4.78 g, 2.9 ml, 31.2 mmol) was added. To a stirred suspension of sodium hydride (60% disp; 2.99 g, 74.8 mmol) in dry tetrahydrofuran (100 ml) at room temperature, and under a nitrogen atmosphere, was added a solution of (2R) bornane-2,10-sultam (13.42 g, 62.34 mmol) in dry THF (40 ml). When effervescence ceased the mixture was stirred for 5 m, and then added by cannula to the acid chloride solution. This was stirred at RT overnight then quenched very cautiously at first with half saturated sodium hydrogen carbonate solution (500 ml). The organic phase was separated and the aqueous extracted with ethyl acetate (2×200 ml). The combined organic extract was washed with half saturated sodium hydrogen carbonate solution (50 ml), brine (500 ml), dried over $MgSO_4$ and the solvent evaporated in vacuo to give a yellow foamy solid. Flash column chromatography ($SiO_2$; EtOAc/hexane, 1:1) furnished the product, compound (20) (Table 3) as a pale yellow solid (17.73 g, 66.5%). A portion of the product 0.413 g was recrystallised from ethanol to give a white crystalline solid (0.341 g).

STEP (F)

To magnesium turnings (1.5 g, 61.6 mmol) under a nitrogen atmosphere at room temperature was added a solution of 3-cyclopentyloxy-4-methoxyphenyl (13.9 g, 51.3 mmol) in dry tetrahydrofuran (10 ml). The mixture was heated to initiate the formation of the Grignard reagent then allowed to reflux. When the reaction subsided the mixture was stirred under reflux for 2 h, diluted with ether/tetrahydrofuran (60 ml; 1:1), cooled to −70° C. and a solution of the α,β-unsaturated olefin (10,0 g, 23.4 mmol) produced in Step E in tetrahydrofuran/ether (150 ml; 1:1) added at such a rate that t he temperature did not exceed −60° C. The reaction was brought to between −30° and −20° C. and stirred for 90 min then quenched at −20° C. with 10% aqueous ammonium chloride solution (100 ml) and extracted with ethyl acetate (200 ml) then (2×100 ml). The combined organic extract was washed with brine (200 ml), dried over $MgSO_4$ and the solvent evaporated in vacuo to give a pale brown clear oil. Flash column chromatography ($SiO_2$; EtOAc/hexane, 1:1 then 3.2) furnished a white crispy foam 13.68 g, 94%. Trituration with hot ethanol/hexane (1:4) (50 ml) followed by recrystallisation from ethanol/hexane (150 ml; 1:3.3) furnished the compound 20 (Tables 1 and 2) as a white fluffy solid (10.92 g, 75.4%).

STEP (G)

To a stirred solution of propane thiol (3.39 g, 4.0 ml, 44.5 mmol) in dry tetrahydrofuran (130 ml) at −10° C. and under a nitrogen atmosphere, was added n-BuLi (1.6M in hexanes; 20.2 ml 32.3 mmol). The mixture was stirred at −10° C. for 30 min and then a solution of the acyl sultam of Step (F) (12.55 g, 20.2 mmol) in dry tetrahydrofuran (100 ml) was added and the reaction maintained at room temperature for 2 h at which time all of the starting material had been consumed (t.l.c.: ethyl acetate/hexane 3:1). The solvent was evaporated in vacuo and ethanol (130 ml) added followed by potassium hydroxide (2.26 g, 40.4 mmol) in water (100 ml). The was stirred under reflux for 2 h then at room temperature overnight. When all of the thioester had been consumed the pH was adjusted with concentrated HCl to 5.5–5.0 and stirred at 60° C. for 2 h (effervescence). The mixture was cooled, concentrated in vacuo and treated with water (200 ml and 10% NaOH solution (80 ml) and extracted with ethyl acetate (4×200 ml). The combined organic extract was washed with sodium hydroxide solution (10%; 2×100 ml), brine (100 ml) then dried over $MgSO_4$ and the solvent evaporated in vacuo. Flash column chromatography ($SiO_2$; ethyl acetate/hexane, 1:1) furnished a clear colourless oil (6.31 g, 82%).

A portion of the oil (1.97 g) was dissolved in ether (50 ml) and treated with ethanolic HCl (10 ml). The mixture was brought to reflux, treated with ether (20 ml), cooled to room temperature, and filtered under a nitrogen stream. The highly hygroscopic white solid was rapidly washed with ether (2×10 ml) and dried under vacuum at 55° C. to give Compound 20 (Tables 4 and 5) as an amorphous white powder (1.62 g, 75%).

EXAMPLES 20–21

Steps (F) and (G) of Example 19 were repeated to yield the compounds 18 and 19 (Tables 4 and 5). The appropriate starting materials of the invention (compounds 18 and 19, Table 3) for Step (F) were obtained as described in Step (E) in Example 19.

EXAMPLE 22

This Example describes the preparation of a compound according to the invention (Step D) and its subsequent conversion (Step D2) to a further compound of the invention.

A 500 ml round-bottomed flask, fitted with a Dean & Stark apparatus was charged with a solution of 3-cyclopentoxy 4-methoxy benzaldehyde (41.6 g, 189 mmol) and ethyl imidazole-4-acetate (24.3 g, 158 mmol; prepared as described in European Patent Specification No. 59156) in glacial acetic acid (100 ml) and dry toluene (230 ml). Ammonium acetate (29.1 g, 78 mmol) was added and the reaction mixture heated under gentle reflux for 18 h. The solvent was removed in vacuo and the residue treated with water (500 ml) and ethyl acetate (1 l). With thorough stirring, sufficient solid sodium hydrogen carbonate was added until effervescence ceased. The phases were separated and the aqueous phase re-extracted with ethyl acetate (2×350 ml). The combined organic extracts were washed with brine (100 ml), dried ($Na_2SO_4$) and evaporated in vacuo to afford a dark oil. This was subjected to chromatography ($SiO_2$; 50% ethyl acetate/hexane→100% ethyl acetate→10% ethanol/ethyl acetate) to afford the imidazolyl ester described in Table 6 as a dark foamy solid (31.4 g, 56%).

A solution of the ester (8.3 g, 23.3 mmol) and triphenylmethyl chloride (7.14 g, 25.6 mmol) in dry pyridine (50 ml) was stirred at room temperature for 3 h under nitrogen. The solvent was removed in vacuo and the residue treated with ethyl acetate (100 ml) and water (100 ml) and the mixture shaken thoroughly. Hexane (100 ml) was added, and the insoluble organic product filtered off with copious water washing and sufficient ether to remove all colour. After sucking to dryness, the triphenylmethylimidazolyl ester described in Table 6 was obtained as a white powder. This material was found to be a 50:50 mix of free base and the corresponding hydrochloride salt.

A solution of the ester (7.9 g, 13.2 mmol) and potassium hydroxide (2.96 g, 52.9 mmol) in 50% aqueous ethanol (140 ml) was heated under gentle reflux for 5 h. The reaction mixture was cooled and the pH adjusted to 6 with concentrated hydrochloric acid. The obtained white precipitate was diluted with water (100 ml) and the product extracted with dichloromethane (total 1 l). The organic extract was dried ($NA_2SO_4$) and evaporated in vacuo affording the carboxylic acid described in Table 6, as an off-white solid (7.4 g, 87%).

STEP (D)

A solution of the acid (4.87 g, 8.5 mmol), 2S-bornane-10,2-sultam (3.67 g, 17.1 mmol), 4-methyl-morpholine (1.03 g, 10.2 mmol), and 4-dimethylaminopyridine (0.52 g, 4.3 mmol) in dry dichloromethane (120 ml) was stirred under $N_2$ for two days. The reaction mixture was partitioned between dischloromethane (150 ml) and 10% aqueous potassium dihydogen-phosphate (150 ml). The phases were separated and the aqueous phase re-extracted with dichloromethane (2×100 ml). The combined organic extracts were washed with 10% aqueous $KH_2PO_4$ (100 ml) and the phases separated. The combined aqueous washed were extracted with dichloromethane (50 ml). All the organic extracts were combined, washed with brine (75 ml), dried ($Na_2SO_4$) and evaporated in vacuo to afford the crude product as a yellow foam (8.9 g). Purification by flash chromatography ($SiO_2$; 70% ether/hexane→100% ether) afforded the triphenylmethylimidazolyl acyl sultam described in Table 6, as a yellow foam (4.5 g, 67%).

STEP (D2)

Dimethylsulphate (129 µl≡172 mg, 1.36 mmol) was added to an ice-cooled solution of the acyl sultam (1 g, 1.30 mmol) in dry acetonitrile (15 ml), and the reaction mixture stirred at room temperature for 18 h. The solvent was removed in vacuo to afford the crude N-methyl imidazolium salt as a yellow foamy solid, This product was dissolved in ethanol (20 ml) and heated under gentle reflux for 45 min. The solvent was removed in vacuo, then partitioned between sat, aqueous $NaHCO_3$ (50 ml) and ethyl acetate (50 ml). The phases were separated and the aqueous phase re-extracted with ethyl acetate (2×30 ml). The combined organic extracts were washed with brine (20 ml), dried ($Na_2SO_4$) and evaporated in vacuo to afford a yellow foam. Purification by flash chromatography ($SiO_2$, 50% ethyl acetate/hexane→100% ethyl acetate) yielded the N-methyl imidazolyl acyl sultam described in Table 6, as a pale yellow foam (550 mg, 78%).

(STEP E)

To an ice-bath cooled, stirred solution of the acyl sultam of Step (D2) (260 mg, 0.48 mmol) in dry tetrahydrofuran (10 ml) was added dropwise phenyl-magnesium bromide (1 m in tetrahydrofuran, 1 ml) under a nitrogen atmosphere. The pale yellow clear solution was stirred for 30 min then quenched with 10% aqueous $NH_4Cl$ (30 ml). The phases were separated and the aqueous phase re-extracted with ethyl acetate (25 ml). The combined organic extracts were washed with brine (5 ml), dried ($Na_2SO_4$) and evaporated in vacuo to afford the crude product as a foamy solid (340 mg). Recrystallisation from ethyl acetate/hexane afforded the pure phenyl acyl sultam described in Table 6, as a white powder (120 mg, 40%).

EXAMPLE 23

The process of Example 1 was repeated using 3-cyclopentylthio-4-methoxybenzaldehyde in place of 3-cyclopentyloxy-4-methoxybenzaldehyde in Step A. Table 7 describes the resulting thioethers formed in the process according to the invention.

TABLE 1
SELECTED $^{1}H$ n.m.r. DATA FOR ACYL SULTAMS
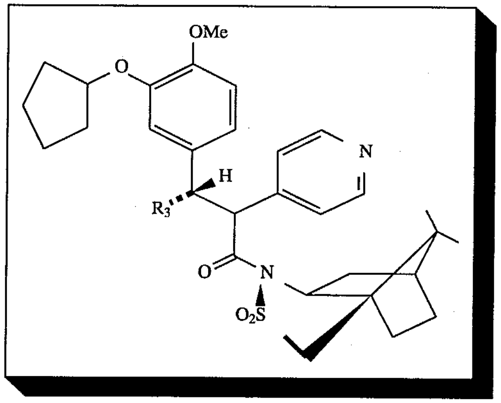
| Compound no. | $R_3$ | γ MeCMe | γ $SO_2CH_2$ | γ OMe | γ CHCHpy | γ OCH | γ CHCHpy | β py $H_3H_5$ | γ py $H_2H_6$ |
|---|---|---|---|---|---|---|---|---|---|
| 1 | 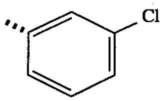 | 0.76(s)<br>0.90(s) | 3.34(d, J 13.5Hz)<br>3.48(d, J 13.5Hz) | 3.70(s) | 4.55(d, J 11.6Hz) | 4.60(br m) | 5.04(d, J 11.6Hz) | 7.36(d, J 6Hz) | 8.40(d, J 6Hz) |
| 2 | 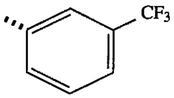 | 0.54(s)<br>0.87(s) | 3.35(d, J 13.5Hz)<br>3.42(d, J 13.5Hz) | 3.70(s) | 4.62(d, J 11.6Hz) | 4.60(br m) | 5.12(d, J 11.5Hz) | 7.39(d, J 6.2Hz) | 8.42(d, J 6.2Hz |
| 3 | 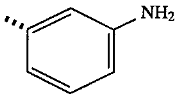 | 0.87(s)<br>0.90(s) | 3.32(d, J 13.8Hz)<br>3.47(d, J 13.8Hz) | 3.69(s) | 4.45(d, J 11.5Hz) | 4.57(br m) | 5.00(d, J 11.5Hz) | 7.30(dd, J 4.6, 1.5Hz) | 8.37(dd, J 4.6, 1.5Hz) |
| 4 | 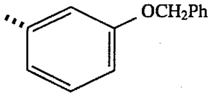 | 0.77(s)<br>0.89(s) | 3.32(d, J 13.8Hz)<br>3.45(d, J 13.8Hz) | 3,70(s) | 4.54(d, J 11.5Hz) | 4.6(br m) | 5.11(d, J 11.5Hz) | 7.34(dd, J 5.0, 1.5Hz) | 8.40(dd, J 5.0, 1.5Hz) |
| 5 | 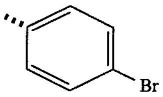 | 0.72(s)<br>0.90(s) | 3.32(d, J 16Hz)<br>3.48(d, J 16Hz) | 3.70(s) | 4.55(d, J 8Hz) | 4.55(br m) | 5.05(d, J 8Hz) | 7.35(m) | 8.4(d, J 6Hz) |

TABLE 1-continued

SELECTED [1]H n.m.r. DATA FOR ACYL SULTAMS

| Compound no. | $R_3$ | γ MeCMe | γ $SO_2CH_2$ | γ OMe | γ CHCHpy | γ OCH | γ CHCHpy | β py $H_3H_5$ | γ py $H_2H_6$ |
|---|---|---|---|---|---|---|---|---|---|
| 6 | 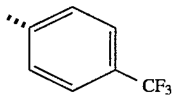 | 0.62(s)<br>0.89(s) | 3.33(d, J 14.9Hz)<br>3.35(d, J 14.9Hz) | 3.70(s) | 4.63(d, J 10.3Hz) | 4.60(br m) | 5.10(d, J 10.3Hz) | 7.38(d, J 7.4Hz) | 8.4(d, J 7.4Hz) |
| 7 | 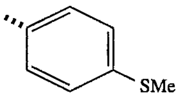 | 0.72(s)<br>0.89(s) | 3.32(d, J 14.9Hz)<br>3.45(d, J 14.9Hz) | 3.67(s) | 4.53(d, J 11.5Hz) | 4.59(br m) | 5.04(d, J 11.5Hz) | 7.34(dd, J 4.5, 1.5Hz) | 8.39(d, J 4.5, 1.5Hz) |
| 8 | 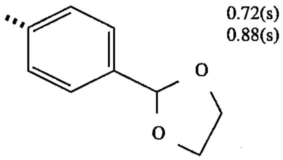 | 0.72(s)<br>0.88(s) | 3.30(d, J 16Hz)<br>3.45(d, J 16Hz) | 3.68(s) | 4.55(d, J 13Hz) | 4.55(br m) | 5.08(d, J 13Hz) | 7.5(d, J 8Hz) | 8.48(d, J 8Hz) |
| 9 | 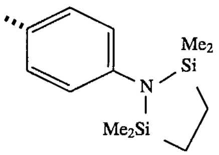 | 0.87(s)<br>0.90(s) | 3.32(d, J 13.7Hz)<br>3.46(d, J 13.7Hz) | 3.70(s) | 4.44(d, J 11.5Hz) | 4.59(br m) | 4.98(d, J 11.Hz) | 7.3(m) | 8.37(d, J 5.8Hz) |
| 10 | 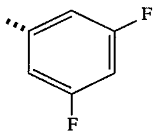 | 0.87(s)<br>0.92(s) | 3.36(d, J 13.8Hz)<br>3.51(d, J 13.8Hz) | 3.71(s) | 4.53(d, J 11.6Hz) | 4.55(br m) | 5.01(d, J 11.6Hz) | 7.29(d, J 5.7Hz) | 8.40(d, J 5.7Hz) |
| 11 | 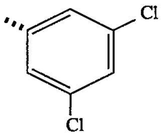 | 0.75(s)<br>0.90(s) | 3.35(d, J 16Hz)<br>3.5(d, J 16Hz) | 3.7(s) | 4.57(d, J 8Hz) | 4.6(br m) | 5.1(d, J 8Hz) | 7.32(d, J 6Hz) | 8.4(d, J 6Hz) |
| 12 | 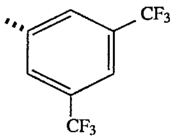 | 0.35(s)<br>0.85(s) | 3.33(d, J 15Hz)<br>3.44(d, J 15Hz) | 3.71(s) | 4.77(d, J 11.7Hz) | 4.65(br m) | 5.11(d, J 11.7Hz) | 7.43(d, 6Hz) | 8.42(d, J 6Hz) |

TABLE 1-continued
| | | SELECTED $^1H$ n.m.r. DATA FOR ACYL SULTAMS | | | | | | | |
|---|---|---|---|---|---|---|---|---|---|
| Compound no. | $R_3$ | γ MeCMe | γ $SO_2CH_2$ | γ OMe | γ CHCHpy | γ OCH | γ CHCHpy | β py $H_3H_5$ | γ py $H_2H_6$ |
| 13 | 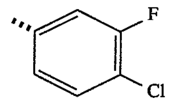 | 0.73(s)<br>0.91(s) | 3.35(d, J 16Hz)<br>3.4(d, J 16Hz) | 3.7(s) | 4.55(d, J 9Hz) | 4.6(br m) | 5.05(d, J 9Hz) | 7.32(d, J 6Hz) | 8.40(d, J 6Hz) |
| 14 | 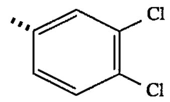 | 0.7(s)<br>0.9(s) | 3.35(d, J 13Hz)<br>3.5(d, J 13Hz) | 3.75(s) | 4.58(d, J 8Hz) | 4.65(br m) | 5.2(d, J 8Hz) | 7.38(d, J 6Hz) | 8.41(d, J 6Hz) |
| 15 | 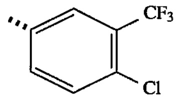 | 0.55(s)<br>0.90(s) | 3.42(d, J 13.8Hz)<br>3.48(d, J 13.8Hz) | 3.7(s) | 4.65(d, J 13Hz) | 4.6(br m) | 5.1(d, J 13Hz) | 7.39(m) | 8.41(d, J 8Hz) |
| 16 | 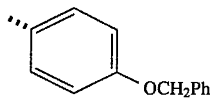 | 0.69(s)<br>0.87(s) | 3.31(d, J 13.8Hz)<br>3.44(d, J 13.8Hz) | 3.69(s) | 4.52(d, J 11.5Hz) | 4.55(br m) | 5.01(obscured d) | 7.36(m) | 8.38(d, J 6.1Hz) |
| 17 | 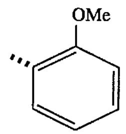 | 0.85(s)<br>1.00(s) | 3.32(d, J 17.4Hz)<br>3.45(d, J 17.4Hz) | 3.78(s) | 5.72(m) | 4.55(br m) | 5.72(m) | 7.25(dd, J 8.7, 1.5Hz) | 8.35(dd, J 8.7, 1.5Hz) |
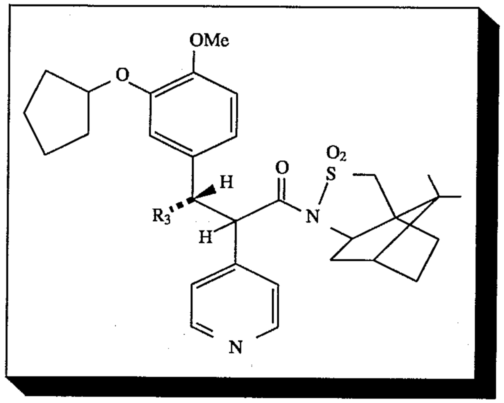

TABLE 1-continued
| SELECTED $^1H$ n.m.r. DATA FOR ACYL SULTAMS | | | | | | | | | |
|---|---|---|---|---|---|---|---|---|---|
| Compound no. | $R_3$ | γ MeCMe | γ $SO_2CH_2$ | γ OMe | γ CHCHpy | γ OCH | γ CHCHpy | β py $H_3H_5$ | γ py $H_2H_6$ |
| 18 | 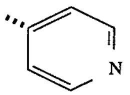 | 0.67(s)<br>0.88(s) | 3.34(d, J 13.4Hz)<br>3.47(d, J 13.4Hz) | 3.78(s) | 4.59(d, J 11.6Hz) | 4.8(br m) | 5.09(d, J 11.6Hz) | 7.06(dd, J 4.5, 1.6Hz)<br>7.39(dd, J 4.5, 1.6Hz) | 8.34(dd, J 4.5, 1.6Hz)<br>8.41(dd, J 4.5, 1.6Hz) |
| 19 | 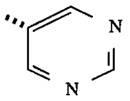 | 0.65(s)<br>0.90(s) | 3.35(d, J 13.5Hz)<br>3.44(d, J 13.5Hz) | 3.80(s) | 4.63(d, J 11.6Hz) | 4.7(br m) | 5.12(d, J 11.6Hz) | 7.38(d, J 4.5Hz) | 8.45(d, J 4.5Hz) |
| 20 | 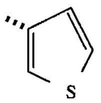 | 0.65(s)<br>0.86(s) | 3.30(d, J 13.7Hz)<br>3.41(d, J 13.7Hz) | 3.78(s) | 4.68(d, J 11.4Hz) | 4.8(br m) | 4.96(d, J 11.4Hz) | 7.39(dd, J 4.5, 1.6Hz) | 8.42(dd, J 4.5, 1.6Hz) |

TABLE 2

SELECTED DATA FOR ACYL SULTAMS

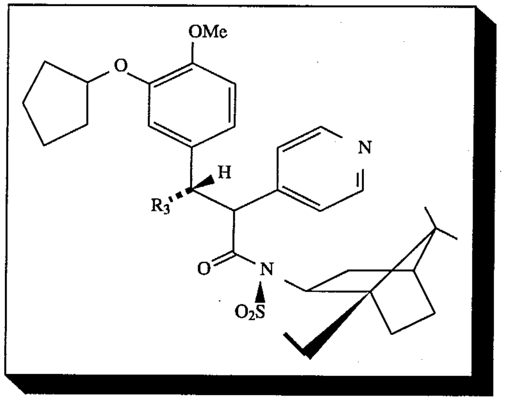

| Compounnd no. | $R_3$ | Description | m.p(°C.) | CHN Analysis Required(Found) | m/z | OR |
|---|---|---|---|---|---|---|
| 1 | 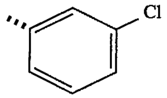 | Off-white solid | 263–265 | $C_{36}H_{41}ClN_2O_5S.0.5H_2O$ requires: C, 65.64; H, 6.43; N, 4.26 (Found: C, 65.53; H, 6.12; N, 4.09%) | (ESI)6.19($M^+$+H, 100%) | +116.3° ($CHCl_3$, 0.42) |
| 2 | 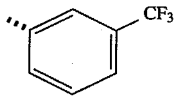 | Off-white solid | | $C_{37}H_{41}F_3N_2O_5S$ requires: C, 64.99; H, 6.19; N, 4.10 (Found: C, 64.53; H, 6.02; N, 3.72%) | (ESI)6.49($M^+$+H, 100%) | |
| 3 | 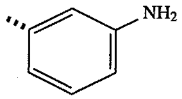 | Off-white solid | 275–277 | $C_{36}H_{41}N_3O_5S.0.25H_2O$ requires: C, 68.38; H, 6.62; N, 6.65 (Found: C, 68.36; H, 6.91; N, 6.57%) | (ESI)6.30($M^+$+H, 16%), 296(100), 228(75) | +146.0° ($CHCl_3$, c 0.48) |
| 4 | 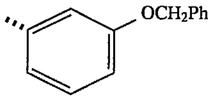 | Pale yellow solid | 180–1822 | $C_{43}H_{47}N_2O_6S$ requires: C, 71.77; H, 6.54; N, 3.89 (Found: C, 71.31; H, 6.71; N, 3.63%) | (EI): 720($M^+$, 12%), 387(100, 319 (38,)227(16) | +103.5° ($CHCl_3$, c 0.96) |
| 5 | 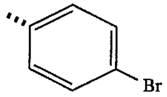 | White solid | 237–239 | | | +90° ($CHCl_3$, c 0.49) |

TABLE 2-continued
| SELECTED DATA FOR ACYL SULTAMS | | | | | | |
|---|---|---|---|---|---|---|
| Compounnd no. | $R_3$ | Description | m.p(°C.) | CHN Analysis Required(Found) | m/z | OR |
| 6 | 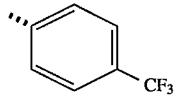 | Off-white solid | | | (EI): 692($M^+$, 3%), 362(19), 359 (100), 281(52), 219(52) | |
| 7 | 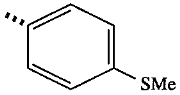 | White solid | 221–223 | $C_{37}H_{44}N_2O_5O_5S_2$ requires: C, 66.45; H, 6.86; N, 3.97 (Found: C, 66.17; H, 6.67; N, 4.11%) | | |
| 8 | 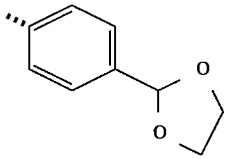 | White solid | 192–193 | | (EI)686($M^+$, 3%), 354(22), 353 (100),265(26), 213(61) | |
| 9 | 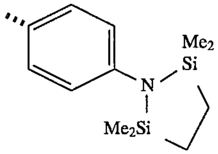 | Off-white crystals | 211–212.5 | | (EI)771($M^+$, 12%), 529(27), 438 (100), 370(20) | |
| 10 | 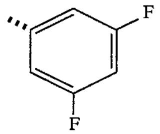 | White solid | 262–263 | $C_{36}H_{40}F_2N_2O_5S$ requires: C, 66.44; H,6.20; N, 4.30 (Found: C, 66.00; H, 6.21; N, 4.23%) | (EI)651($M^+$+H, 100%) | |
| 11 | 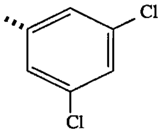 | White solid | 255–257 | | (EI)682($M^+$, 6%), 351(62), 349 (100),283(59), 265(14) | +99.0° ($CHCl_3$, 0.41) |

TABLE 2-continued
| Compounnd no. | $R_3$ | Description | m.p(°C.) | CHN Analysis Required(Found) | m/z | OR |
|---|---|---|---|---|---|---|
| | | | SELECTED DATA FOR ACYL SULTAMS | | | |
| 12 | 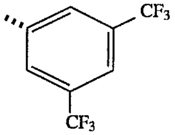 | pale yellow solid | | | | |
| 13 | 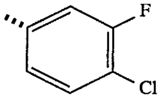 | White solid | | | | |
| 14 | 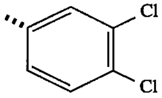 | White solid | 266–267.5 | | (EI): 682(M+, 3%), 353(11), 349 (100), 283(52), 281(82) | |
| 15 | 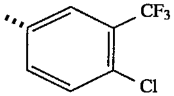 | Off-white solid | 251–253 | | (EI): 716(M+, 5%),305(29), 383(82), 315(100), 241(31) | |
| 16 | 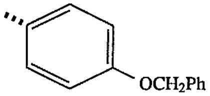 | White solid | 194–195.5 | | | +104.9° ($CHCl_3$, 0.33) |
| 17 | 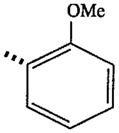 | White solid | 199–200 | | (EI): 644(M+, 2%), 254(100) | +176.9° ($CHCl_3$, 0.46) |

TABLE 2-continued
SELECTED DATA FOR ACYL SULTAMS
| Compounnd no. | $R_3$ | Description | m.p(°C.) | CHN Analysis Required(Found) | m/z | OR |
|---|---|---|---|---|---|---|
| | | | 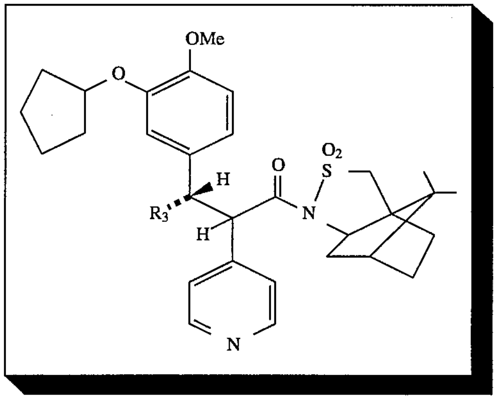 | | | |
| 18 | 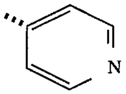 | White solid | | | | |
| 19 | 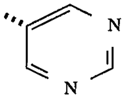 | White solid | | | | |
| 20 | 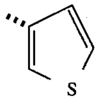 | Fluffy white solid | 133–137 | $C_{34}H_{40}N_2O_5S_2$ requires: C, 65.78; H, 6.49; N, 4.51 (Found: C, 65.57; H, 6.50; N, 4.45%) | | –46.7° ($CH_2Cl_2$, c 1.03) |

TABLE 3

SELECTED DATA FOR UNSATURATED ACYL SULTAMS

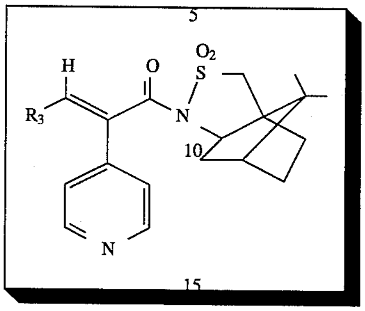

| Compound no. | $R_3$ | Description | m.p (°C.) | CHN Analysis Required(Found) | m/z | OR | $^1$H n.m.r. |
|---|---|---|---|---|---|---|---|
| 18 | 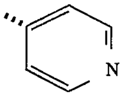 | White solid | | | | | 1.03(3H, s), 1.29(3H, s), 1.42(2H, m), 1.99(3H, m), 2.11(2H, J 6.2Hz), 3.47(1H, d, J13.7Hz), 3.59(1H, d, J 13.7Hz), 4.06(1H, t, J 6.2Hz), 6.97(2H, dd, J 5.0, 1.6Hz), 7.24(1H, s), 7.28 (2H, dd, J 4.4, 1.6Hz), 8.46(2H, dd, J 4.5, 1.6 Hz), and 8.57(2H, dd, J 4.5, 1.6Hz) |
| 19 | 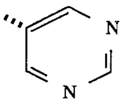 | White solid | | | | | 1.04(3H, s), 1.29(3H, s), 1.50(2H, m), 1.9–2.1 (3H, m), 2.12(2H, d, J 6.2Hz), 3.47(1H, d, J 13.7Hz), 3.60(1H, d, J 13.7Hz), 4.07(1H, t, J 6.2Hz), 7.21(1H, s), 7.61(2H, dd, J 4.4, 1.6 Hz), 8.45(2H, s), 8.61(2H, dd, J 4.4, 1.6Hz), and 9.05(1H, s) |
| 20 | 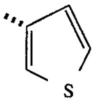 | White crystalline solid | 205–209 | $C_{22}H_{24}N_2O_3S_2$ requires: C, 61.66; H, 5.64; N, 6.54 (Found: C, 61.49; H, 5.66; N, 6.46) | (EI): 428($M^+$, 8%), 215(18), 214(94), 186(100), 158(12), 115(44) | +5.2° ($CH_2Cl_2$, c 1.03) | 1.03(3H, s), 1.33(3H, s), 1.3–1.45(2H, m), 1.8–2.0(2H, m), 2.07(2H, br d, J 6.2Hz), 3.51(2H, dd, J 23.3, 13.7Hz) 4.08(1H, t, J 6.2Hz), 6.58 (1H, dd, J 5.1, 1.2Hz), 7.11(1H, dd, J 5.1, 2.9 Hz), 7.22(1H, m), 7.37(2H, dd, J 4.5, 1.6Hz), and 8.63(2H, dd, J 4.5, 1.6 Hz) |

TABLE 4
SELECTED $^1$H n.m.r DATA FOR TRIARYLETHANES
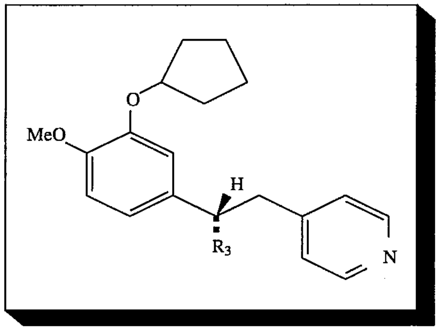
| Compound no. | $R_3$ | Salt form | δ $(CH_2)_4$ | δ CHC $H_2$py | δ OMe | δ $CHCH_2$py | δ OC H | δ py $H_3H_5$ | δ py$H_2H_6$ |
|---|---|---|---|---|---|---|---|---|---|
| 1 | 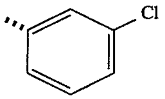 | Base | 1.5–1.9(br m) | 3.55(d, J 7.9Hz) | 3.80(s) | 4.16(t, J 7.9Hz) | 4.65(br m) | 7.49(br s) | 8.56(br s) |
| 2 | 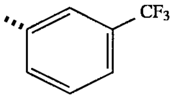 | HCl ($d_6$-dmso) | 1.2–1.9(br m) | 3.3–3.5(m) | 3.65(s) | 4.11(t, J 7Hz) | 4.75(br m) | 7.45–7.55(m) | 8.65(d, J 4.5Hz) |
| 3 | 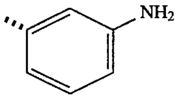 | Base | 1.55–1.8(br m) | 3.26(br d, J 8Hz) | 3.78(s) | 4.03(br t, J 8Hz) | 4.65(br m) | 6.92(d, J 5.8Hz) | 8.37(d, J 5.8Hz) |
| 4 | 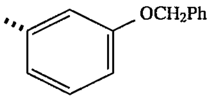 | Base | 1.5–2.0(br m) | 3.29(d, J 7.1Hz) | 3.80(s) | 4.11(t, J 7.1Hz) | 4.65(br m) | 6.9(dd, J 4.5, 1.6Hz) | 8.38(d, J 4.5, 1.6Hz) |
| 5 | 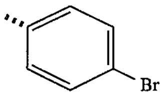 | HCl | 1.5–1.9(br m) | 3.54(d, J 8.5Hz) | 3.80(s) | 4.16(t, J 8.5Hz) | 4.65(br m) | 7.52(d, J 6Hz) | 8.55(d, J 6Hz) |

TABLE 4-continued
SELECTED $^1$H n.m.r DATA FOR TRIARYLETHANES
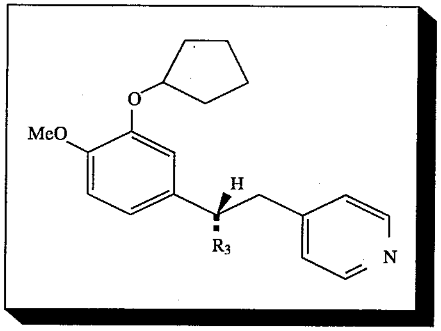
| Compound no. | $R_3$ | Salt form | δ $(CH_2)_4$ | δ CHC $H_2$py | δ OMe | δ $CHCH_2$py | δ OC H | δ py $H_3H_5$ | δ py$H_2H_6$ |
|---|---|---|---|---|---|---|---|---|---|
| 6 | 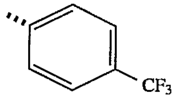 | HCl | 1.4–1.9(br m) | 3.28(d, J 8.3Hz) | 3.75(s) | 4.19(t, J 8.3Hz) | 4.65(br m) | 6.91(d, J 6.6Hz) | 8.36(d, J 6.6Hz) |
| 7 | 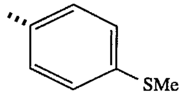 | HCl | 1.5–2.0(br m) | 3.54(d, J 8.0Hz) | 3.80(s) | 4.13(t, J 7.8Hz) | 4.65(br m) | 7.47(d, J 6.6Hz) | 8.52(d, J 6.6Hz) |
| 8 | 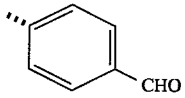 | Base | 1.5–1.9(br m) | 3.32(ckl, J 8, <2Hz) | 3.80(s) | 4.22(t, J 8Hz) | 4.65 (br m) | 7.78(d, J 8.5Hz) | 8.4(d, J 8.5Hz) |
| 9 | 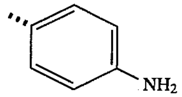 | 2HCl ($d_4$-MeOH) | 1.6–1.8(br m) | 37–38(m) | 3.75(s) | 4.56(t, J 8.8Hz) | 4.75(br m) | 7.91(d, J 6.6Hz) | 8.65(d, J 6.6Hz) |
| 10 | 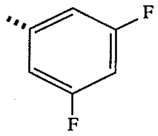 | HCl | 1.6–1.8(br m) | 3.55(br d, J 7.0Hz) | 3.81(s) | 4.18(t, J 8.3Hz) | 4.65 (br m) | 7.53(d, J 5Hz) | 8.62(d, J 5Hz) |

TABLE 4-continued
SELECTED $^{1}H$ n.m.r DATA FOR TRIARYLETHANES
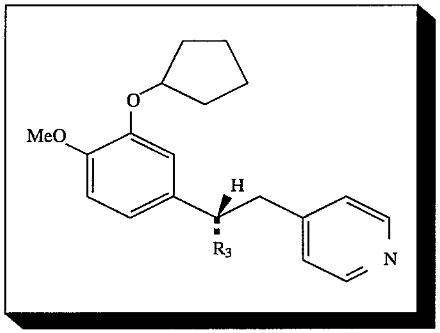
| Compound no. | $R_3$ | Salt form | δ $(CH_2)_4$ | δ CHC $H_2$py | δ OMe | δ $CHCH_2$py | δ OC H | δ py $H_3H_5$ | δ py$H_2H_6$ |
|---|---|---|---|---|---|---|---|---|---|
| 11 | 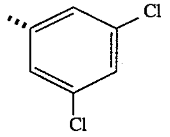 | HCl | 1.5–1.9(br m) | 3.52(m) | 3.80(s) | 4.15(t, J 8.5Hz) | 4.65 (br m) | 7.57(d, J 6.5Hz) | 8.6(d, J 6.5Hz) |
| 12 | 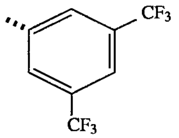 | HCl | 1.5–1.9(br m) | 3.63(br d, J 6.9Hz) | 3.81(s) | 4.35(t, J 6.9Hz) | 4.65 (br m) | 7.55(d, J 6Hz) | 8.61(d, J 6Hz) |
| 13 | 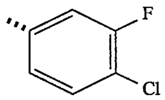 | HCl | 1.5–1.9(br m) | 3.54(d, J 8Hz) | 3.81(s) | 4.17(t, J 8Hz) | 4.75 (br m) | 7.49(d, J 6Hz) | 8.57(d, J 6Hz) |
| 14 | 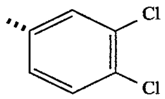 | HCl | 1.5–1.9(br m) | 3.53(d, J 8Hz) | 3.80(s) | 4.15(t, J 9Hz) | 4.65 (br m) | 7.52(d, J 6Hz) | 8.58(d, J 6Hz) |
| 15 | 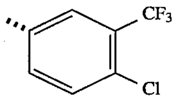 | HCl | 1.5–1.9(br m) | 3.56(d, J 8Hz) | 3.8(s) | 4.25(t, J 8Hz) | 4.7(br m) | 7.53(d, J 6Hz) | 8.60(d, J 6Hz) |

TABLE 4-continued
SELECTED $^1H$ n.m.r DATA FOR TRIARYLETHANES
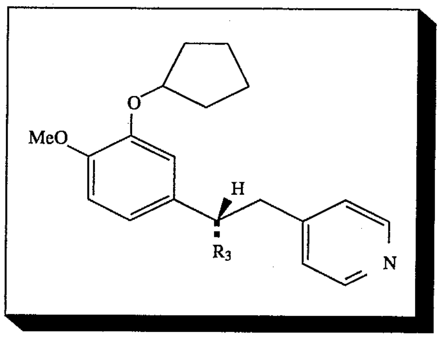
| Compound no. | $R_3$ | Salt form | δ $(CH_2)_4$ | δ CHC $H_2py$ | δ OMe | δ $CHCH_2py$ | δ OC H | δ py $H_3H_5$ | δ $pyH_2H_6$ |
|---|---|---|---|---|---|---|---|---|---|
| 16 | 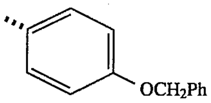 | Base | 1.5–2.1(br m) | 3.27(d, J 7.8Hz) | 3.79 | 4.10(t, J 7.8Hz) | 4.65 (br m) | 7.39(d, J 7.6Hz) | 8.38(d, J 7.6Hz) |
| 18 | 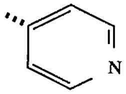 | 2HCl ($d_4$-MeOH) | 1.5–1.9(br m) | 3.91(m) | 3.74(s) | 4.92(dd, J 9.5, 7.1Hz) | 4.75(br m) | 7.99(d, J 6.8Hz)<br>8.17(d, J 6.7Hz) | 8.70(d, J 6.8Hz)<br>8.79(d, J 6.8Hz) |
| 19 | 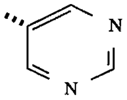 | HCl | 1.5–1.95(br m) | 3.83(d, J 7.3Hz)<br>3.85(d, J 8.7Hz) | 3.75(s) | 4.64(d, J 8.7Hz)<br>4.65(d, J 7.3Hz) | 4.80(br m) | 7.05(d, J 6.7Hz) | 8.69(d, J 6.7Hz) |
| 20 | 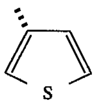 | HCl | 1.5–1.9(br m) | 3.46(dd, J 13.3, 9.0Hz)<br>3.61(dd, J 13.3, 9.0Hz) | 3.80(s) | 4.2(t, J 7.9Hz) | 4.65 (br m) | 7.46(d, J 7.5Hz) | 8.55(d, J 6.5Hz) |

TABLE 5

SELECTED DATA FOR TRIARYLETHANES

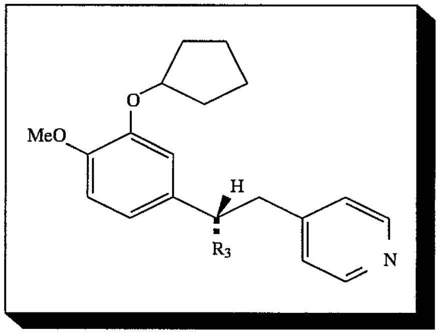

| Compound no | $R_3$ | Salt form | Description | m.p.(°C.) | CHN Analysis Required (Found) | m/z | OR |
|---|---|---|---|---|---|---|---|
| 1 | 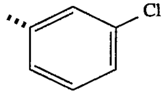 | HCl | White solid | | $C_{25}H_{26}ClN_2O_2$ HCl 0.2 $H_2O$ requires: C, 67.02; H, 6.16; N, 3.13 (Found: C, 67.01; H, 6.15; 3.05%) | (El): 407($M^+$+6%), 339(6), 315(21), 247(100) | |
| 2 | 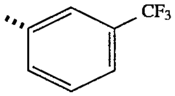 | HCl | Pale yellow solid | | | (El): 441($M^+$,5%), 349(8), 281(100) | |
| 3 | 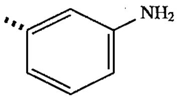 | 2HCl | Off-white solid | 220–222 (dec) | $C_{25}H_{28}N_2O_2$, 2HCl, 0.8$H_2O$ requires: C, 63.10; H, 6.48; N, 5.89 (Found: C, 63.07; H, 6.41; N, 5.82%) | (El): 388($M^+$, 15%), 296(76), 220 (100), 196(25), 167(25) | 140.3° (MeOH, c 0.31) |
| 4 | 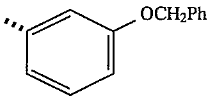 | HCl | Pale yellow solid | | $C_{32}H_{32}NO_3$, HCl, 0.8$H_2O$ requires: C, 72.59; H, 6.59; N, 2.64 (Found: C, 72.58; H, 6.69; N, 2.51%) | (ESl): 443($M^+$+2, 2.1%), 442($M^+$+1.87), 350(22), 349(100), 281(40), 250(30) | +14.6° (MeOH, c 0.51) |
| 5 | 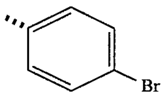 | HCl | Pale yellow foam | | | | |

TABLE 5-continued

SELECTED DATA FOR TRIARYLETHANES

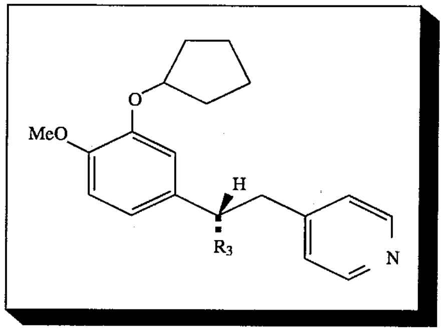

| Compound no | $R_3$ | Salt form | Description | m.p.(°C.) | CHN Analysis Required (Found) | m/z | OR |
|---|---|---|---|---|---|---|---|
| 6 | 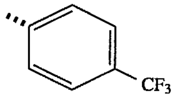 | HCl | Pale yellow solid | 157–158 | $C_{26}H_{26}NO_3$, HCl, $0.2H_2O$ requires: C, 64.85; H, 5.74; N, 2.91 (Found: C, 64.80; H, 5.71; N, 3.03%) | | +47.9 ($CHCl_3$, c 0.28) |
| 7 | 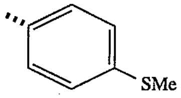 | HCl | White crystalline solid | 191–193 | $C_{26}H_{29}NO_2S$, HCl requires: C, 68.48; H, 6.63; N, 3.07 (Found: C, 68.42; H, 6.66; N, 3.05%) | (EI): 420($M^+$, 0%), 215(18), 214(9.1), 186(100), 150(12), 115(44) | +10.7° (EtOH, c 0.55) |
| 8 | 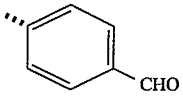 | Base | Pale yellow oil | | | (EI): 401($M^+$, 5%), 309(15), 242(10), 241(100), 153(11), 152(11) | +5.0° ($CHCl_3$, 0.32) |
| 9 | 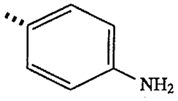 | 2HCl | While solid | 80–85 | $C_{25}H_{28}N_2O_2$2HCl $0.5H_2O$ requires: C, 63.83; H, 6.61, N, 5.96 (Found: C, 63.85, H, 6.54, N, 5.81%) | (EI): 389($M^+$, 5%), 296(100), 229(12) | +13.6° ($CHCl_3$, 0.50) |
| 10 | 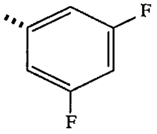 | HCl | Pale yellow solid | | $C_{25}H_{25}F_2NO_2$ HCl, $0.3H_2O$ requires: C, 66.53; H, 5.94; N, 3.10 (Found: C, 66.28; H, 5.91; N, 2.99%) | (EI): 409($M^+$, 11%), 341(20), 317 (19), 249(100). | +160.6° ($CHCl_3$, 0.40) |

TABLE 5-continued

SELECTED DATA FOR TRIARYLETHANES

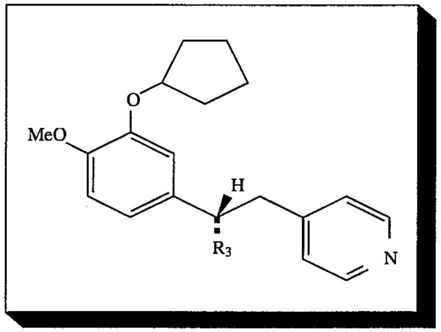

| Compound no | $R_3$ | Salt form | Description | m.p.(°C.) | CHN Analysis Required (Found) | m/z | OR |
|---|---|---|---|---|---|---|---|
| 11 | 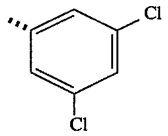 | HCl | Pale yellow solid | | $C_{25}H_{26}Cl_2NO$ HCl $0.4H_2O$ requires: C, 61.78; H, 5.56; N, 2,88 (Found: C, 61.73; H, 5.49; N, 2.76%) | (EI): 401($M^+$, 5%), 309(15), 242(10), 241(100), 153(11), 152(14) | +43.3° (EtOH, c 0.24) |
| 12 | 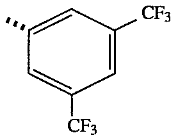 | HCl | Pale yellow solid | | $C_{27}H_{25}F_6NO_2$ HCl, $0.6H_2O$ requires: C, 58.25; H, 4.92; N, 2.52 (Found: C, 58.12; H, 4.68; N, 2.39%) | (EI): 441($M^+$, 10%), 375(11), 373(17), 349(14), 283(64), 281(100) | +05.4° ($CHCl_3$, 0.45) |
| 13 | 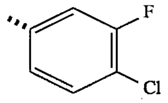 | HCl | Pale yellow foam | | $C_{25}H_{25}ClFNO_2$, HCl, $0.4H_2O$ requires: C, 63.70; H, 5.77; N, 2.97 (Found: C, 63.61; H, 5.54; N, 2.90%) | (EI): 425($M^+$, 6%), 333(16), 217(34), 265(100), 241(14) | +35.4° (EtOH, c 0.22) |
| 14 | 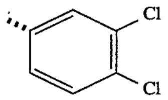 | HCl | Pale yellow foam | | $C_{25}H_{25}Cl_2NO_2$, HCl, $0.3H_2O$ requires: C, 62.01; H, 5.54; N, 2.89 (Found: C, 62.01; H, 5.68; N, 2.86%) | | +30.4° (EtOH, c 0.22) |
| 15 | 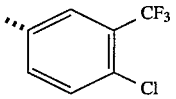 | HCl | Pale yellow foam | | $C_{26}H_{25}ClF_3NO_2$, HCl requires: C, 60.95; H, 5.11; N, 2.73 (Found: C, 60.56; H, 5.06; N, 2.67%) | (EI): 475($M^+$, 10%), 409(16), 383(26), 315(100) | +37.5° (EtOH, c 0.28) |

TABLE 5-continued
SELECTED DATA FOR TRIARYLETHANES
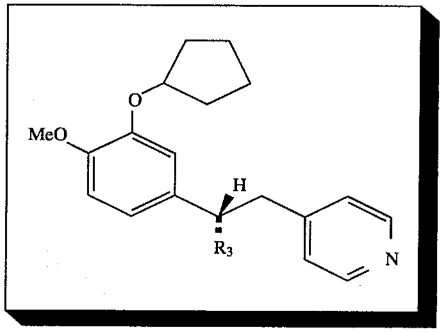
| Compound no | $R_3$ | Salt form | Description | m.p.(°C.) | CHN Analysis Required (Found) | m/z | OR |
|---|---|---|---|---|---|---|---|
| 16 | 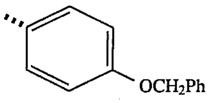 | Base | White solid | | $C_{32}H_{33}NO_3$, requires: C, 80.13; H, 6.93; N, 2.92 (Found: C, 79.78; H, 6.97; N, 2.61%) | | |
| 18 | 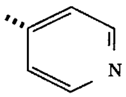 | 2HCl | White solid | 230–233 (dec.) | $C_{24}H_{26}N_2O_2$, 2HCl, requires: C, 64.43; H, 6.31; N, 6.26 (Found: C, 63.97; H, 6.26; N, 6.06%) | (EI): 374($M^+$, 8%), 306(16), 282(11), 214(100) | +55.4° (EtOH, c 0.22) |
| 19 | 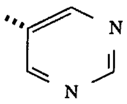 | HCl | White solid | | | (EI): 375($M^+$, 7%), 307(17), 283(11), 215(100) | |
| 20 | 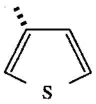 | HCl | While solid | 165–167 (dec.) | $C_{23}H_{25}NO_2S$ HCl, requires: C, 66.42; H, 6.26; N, 3.37 (Found: C, 66.06; H, 6.27; N, 3.26%) | (ES): 380($M^+$+H, 15%), 288(20), 287(100) | +98.3° (EtOH, c 1.17) |

TABLE 6

SELECTED DATA FOR IMIDAZOLE DERIVATIVES

| Compound | Description | m.p.(°C.) | CHN Analysis Required (Found) | m/z | $^1$H n.m.r |
|---|---|---|---|---|---|
| 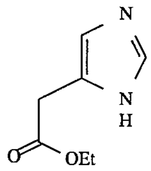 | Dark oil (used crude) | | | | 1.25(3H, t, J 7.2Hz, Me), 3.66(2H, s, $CH_2$imidazole), 4.15(2H, q, J 7.2Hz, $OCH_2$) 6.95(1H, s, imidazole-$H_2$), 7.57(1H, s, imidazole-$H_4$), 8.5(1H, br, s, NH) |
| 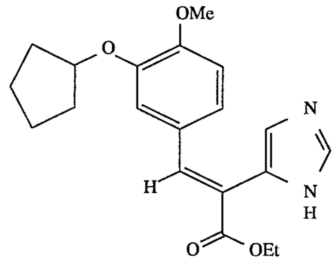 | Dark oil (used crude) | | | | 1.30(3H, t, J 7Hz, $MeCH_2$), 1.4–2.0(8H, m, $(CH_2)_1$), 3.82(3H, s, OMe), 4.27(2H, q, J 7Hz, $CH_2Me$), 4.47(1H, m, OCH), 6.7–6.95(3H, m, ArH), 7.0(1H, s, imidazole-$H_5$), 7.58(1H, s, imidazole-$H_2$), and 7.75(1H, s, HC═C) |
| 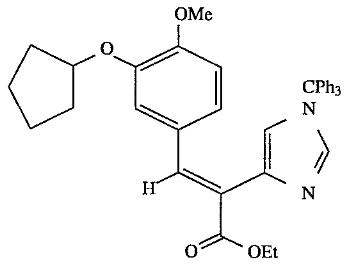 | While solid | | | | 1.27(3H, t, J 7.1Hz, $MeCH_2$), 1.4–1.9(8H, m, $(CH_2)_4$), 3.86(3H, s, OMe), 4.22(2H, q, J 7.1 Hz, $CH_2Me$), 4.52(1H, m, OCH), 6.7–6.85(2H, m, ArH ortho- lo OMe, and cycloponyloxy), 6.89 (1H, dd, J 8.3, 2Hz, ArHpara-cyclopentyl oxy), 6.93(1H, d, J 1.5Hz, imidazole- $H_5$), 7.1–7.2 (6H, m, Ph), 7.25–7.4(9H, m, Ph) 7.50(1H, d, J 1.5Hz, imidazole-$H_2$), and 7.79(1H, s, HC═C) |

TABLE 6-continued

SELECTED DATA FOR IMIDAZOLE DERIVATIVES

| | | | | |
|---|---|---|---|---|
| 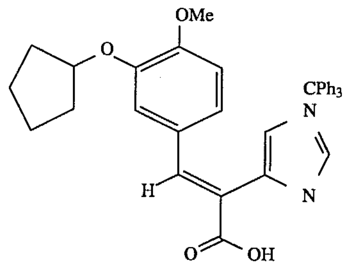 | Off-white solid | | (ESl)571($M^+$+H, 22%), 329(18), 244(95), 243(100) | 1.5–1.9(8H, m, ($CH_2$)$_4$), 2.78(3H, s, OMe), 4.55 (1H, m, OCH), 6.52(1H, d, J 8Hz, ArH ortho to OMe), 6.61(1H, d, J 1.5Hz, ArHortho to cyclopentyloxy), 6.72(1H, d, J 1.5Hz imidazole$H_5$), 6.79(1H, dd, J 8, 1.5Hz, ArH para to cyclo-pentlyoxy), 6.98(6H, m, Ph), 7.3–7.4 (9H, m, Ph), 7.40(1H, d, J 1.5Hz, imidazole-$H_2$), and 7.97(1H, s, HC=C) |
| 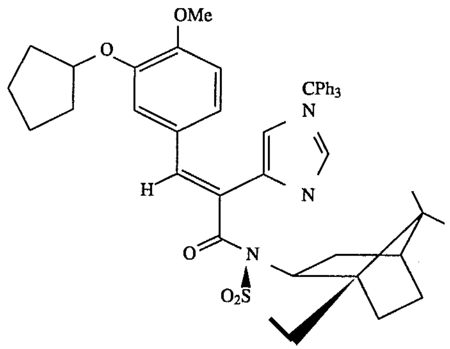 | Pale yellow foam | $C_{47}H_{49}N_3O_5S$ requires: C, 73.51; H, 6.43; N, 5.47 (Found: C, 73.07; H, 6.43; N, 5.37%) | (ESl)767($M^+$+H, 1%), 525(13), 456(19), 243 (98), 165(100) | 0.99(3H, s, MeCMe), 1.25(3H, s, MeCMe), 1.3–2.2 (15H, m, alkyl H), 3.39(1H, d, J 13.7Hz, CHHSO$_2$), 3.47(1H, d, J 13.7Hz, CHHSO$_2$), 3.81(3H, s, OMe(, 4.05(1H, dd, J 6.4Hz, NCH), 4.56(1H, m, CH), 6.66(1H, d, J 8.4Hz, ArH ortho to OMe), 6.72(1H, d, J 1.4Hz, ArH ortho to cyclopentyloxy), 6.89(1H, dd, J 8.4–1.4 Hz, ArH para to cyclopentyloxy), 6.99(1H, d, J 1.5Hz, imidazole-$H_5$), 7.07–7.15(7H, m, HC=C+ Ph), 7.2–7.35(9H, m, Ph), and 7.38(1H, d, J 1.5Hz, imidazole-$H_2$) |

TABLE 6-continued

SELECTED DATA FOR IMIDAZOLE DERIVATIVES

| Compound | Description | m.p.(°C.) | CHN Analysis Required (Found) | OR | m/z | $^1$H n.m.r |
|---|---|---|---|---|---|---|
| 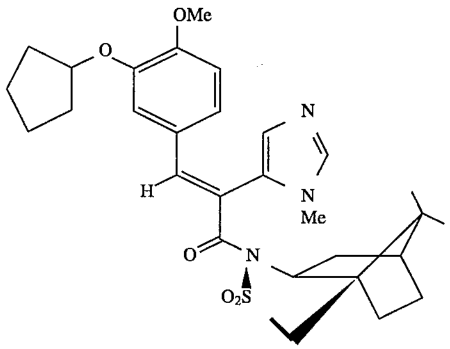 | Pale yellow foam | | $C_{29}H_{37}N_3O_5S$ requires: C, 64.54; H, 6.91; N, 7.79 (Found: C, 64.21; H, 6.96; N, 7.55%) | +46.1 ($CHCl_3$, c 0.40) | (ESI)539($M^+$+H, 57%), 471(74), 229(74), 214 (35), 161(47), 69 (82) | 1.02(3H, s, MeCMe), 1.32(3H, s, MeCMe), 1.3–2.15(15H, m, alkyl H) 3.29(3H, s, MeN), 3.42(1H, d, J 13.6Hz, CHHSO$_2$), 3.54(1H, d, J 13.6Hz, CHHSO$_2$), 3.83(3H, s, OMe), 4.10(1H, app. t, J 6Hz, NCH), 4.37(1H, m, OCH), 6.48(1H, d, J 1.9Hz, ArHoetho to cylcopentyloxy), 6.75(1H, d, J 8.3 Hz, ArH ortho to OMe), 6.81(1H, dd, J 8.3, 1.9Hz, ArHpara to cyclopentyloxy), 7.19(1H, s, imidazole-H$_5$), 7.41(1H, s, HC=C), and 7.48(1H, s, imidazole-H$_2$) |
| 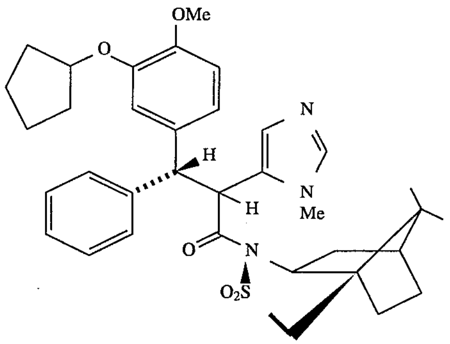 | White solid | 247–249 | $C_{35}H_{43}N_3O_5S$ requires: C, 68.04; H, 7.02; N, 6.80 (Found: C, 67.72; H, 7.05; N, 6.62%) | −181.0° ($CHCl_3$, c 0.36) | (EI)617($M^+$+H, 3%), 282(33), 281(100), 181 (14), 152(12), 95 (16) | 0.66(3H, s, MeCMe), 0.95(3H, s, MeCMe), 1.2–2.1(15H, m, alkyl H), 2.70 (3H, s, MeN)3.36(1H, d, J 13.8Hz, CHHSO$_2$), 3.42(1H, d, J 13.8Hz, CHHSO$_2$), 3.82(3H, s, OMe), 3.84(1H, m, NCH), 4.62(1H, d, J 11.3Hz, CHCHimidazole), 4.77(1H, d, J 11.3Hz, CHCHimidazole), 4.84(1H, m, OCH), 6.8–6.95(4H, m, ArH + imidazole-H$_5$), 7.0–7.15(6H, m, Ph + imidazole-H$_2$) |

TABLE 7
| SELECTED DATA FOR THIOETHER DERIVATIVES | | | | | |
|---|---|---|---|---|---|
| Compound | Description | m.p(°C.) | CHN Analysis Required(Found) | m/z | ¹H n.m.r. |
| 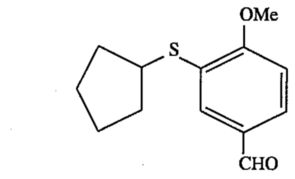 | Pale yellow foam | | | (ESt): 236($M^+$, 70%), 168(100) | 1.55–2.2(8H, br m), 3.65–3.75(1H, m), 3.98(3H, s), 6.95(1H, d, J 5.2Hz), 7.66(1H, dd, J 5.2, 1 Hz), 7.8(1H, d, J 1Hz), and 9.85(1H, s) |
| 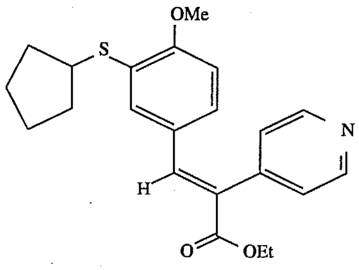 | White crystalline solid | 123–124° | | (ESI): 383($M^+$, 50%), 350(100) | 1.35–1.95(8H, br m), 3.1(1H, q, J 4.2Hz), 3.89 (3H s), 6.68(1H, d, J 2Hz), 6.9(2H, d, J 2Hz), 7.18(2H, d, J 2Hz), 7.85(1H, s), and 6.63(2H, d, J 2Hz) |
| 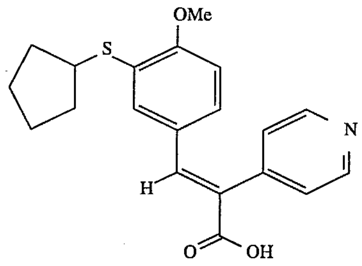 HCl ($d_4$-MeOH) | Yellow solid | | | | 1.3–1.95(8H, br m), 3.15(1H, q), 3.85(3H, s), 6.38(2H, dd, J 2.1Hz), 7.1(1H, d, J 5.2Hz), 7.6 (2H, d, J 2.1Hz), 8.0(1H, s), and 6.67(2H, d, J 2.1Hz) |

TABLE 7-continued
| SELECTED DATA FOR THIOETHER DERIVATIVES | | | | | |
|---|---|---|---|---|---|
| Compound | Description | m.p(°C.) | CHN Analysis Required(Found) | m/z | $^1$H n.m.r. |
| 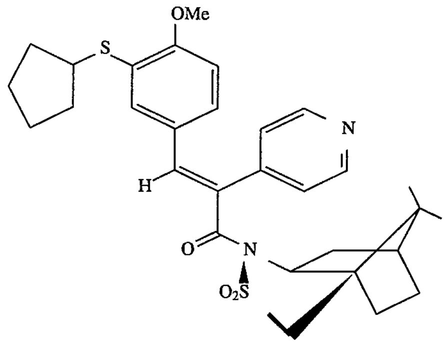 | Pale yellow foam | | | (ESI): 553(M$^+$+H, 10%) | 1.01(3H, s), 1.3(3H s), 1.3–2.15(15H, m), 3.1 (1H, m), 3.45(1H, d, J 3.1Hz), 3.57(1H, d, J 3.1 Hz), 3.81(3H, s), 4.0–4.15(1H, m), 6.68(1H, d, J 3.1Hz), 6.95–7.0(2H, m), 7.25–7.4(3H, m), and 8.56(2H, d, J 2Hz) |
| 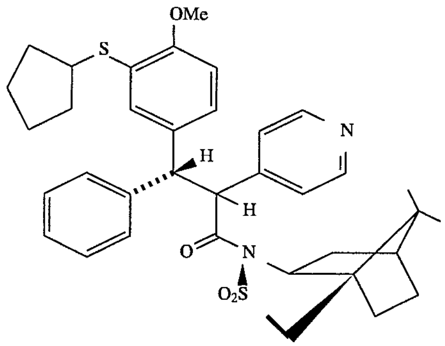 | Off-white foam | | | (Esl): 631(M$^+$+H, 100%) | 0.75(3H, s), 0.93(3H, s), 1.15–2.05(15H, m), 3.33(1H, d, J 3.1Hz), 3.47(1H, d, J 3.1 Hz), 3.4–3.5(1H, m), 3.6–3.75(1H, m), 3.76(3H, s), 4.6(1H, d, J 3.1Hz), 5.09(1H, d, J 3.1Hz), 6.5 (1H, d, J 2.0Hz), 6.85(1H, d, J 2.0Hz), 6.95 (1H, s), 7.0–7.5(5H, m), 7.31(2H, d, J 2.0Hz), and 8.4(2H, d, J 2.0Hz) |

TABLE 7-continued
SELECTED DATA FOR THIOETHER DERIVATIVES
| Compound | Description | m.p(°C.) | CHN Analysis Required(Found) | m/z | $^1$H n.m.r. |
|---|---|---|---|---|---|
| 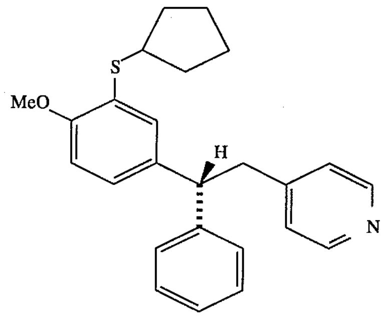 | Pale yellow foam | | | (ESI): 390($M^+$+H, 100%), 297(18) | .4–2.1(8H, br m), 3.2–3.4(2H, m), 3.4–3.6(2H, m), 3.85(3H, s), 6.71(1H, d, J 3.1Hz), 6.8–7.2(9H, m), and 8.38(2H, d, J 2.1Hz) |
| 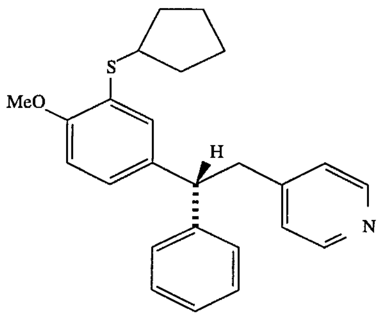 HCl ($d_4$-MeOH) | Pale yellow foam | | $C_{25}H_{27}NOS.HCl.0.6H_2O$ requires: C,68.74; H, 6.74; N, 3.21 (Found: C, 68.72; H, 6.62; N, 3.12%) | | 1.3–2.0(8H, m), 3.5–3.6(1H, m), 3.65 (2H, d, J 3.1Hz), 3.80(3H, s), 4.4(1H, t, J 3.1Hz), 6.85(1H, d, J 2.1Hz), 7.05–7.35(&H, m), 7.8(2H, d, J 2.1Hz), and 8.6(H, d, J 2.1Hz) |

We claim:

1. A compound of formula (1):

Ar—CH=C($R^4$)COAux (1)

wherein each of Ar and $R^4$ is independently an optionally substituted monocyclic aryl group or an optionally substituted bicyclic aryl group, said aryl groups optionally containing one or more heteroatoms selected from the group consisting of oxygen, sulfur and nitrogen atoms; and Aux is the residue of a chiral R- or S-auxiliary.

2. A compound according to claim 1 wherein Aux is the residue of a cyclic or acyclic sultam, alcohol or amine containing one or more homochiral centres.

3. A compound according to claim 2, wherein Aux is the residue of a chiral R- or S-sultam.

4. A compound according to claim 1 wherein Aux is N-(1R)-10,2-bornanesultam or N-(1S)-10,2-bornanesultam.

5. A compound according to claim 1, wherein $R^4$ is an optionally substituted nitrogen-containing monocyclic heteroaryl group.

6. A compound according to claim 5, wherein $R^4$ is an optionally substituted pyridyl group.

7. A compound according to claim 1 wherein Ar is a monocyclic aryl group optionally containing one or more heteroatoms selected from oxygen, sulphur or nitrogen atoms.

8. A compound according to claim 7, wherein Ar is an optionally substituted phenyl group.

9. A compound according to claim 8, wherein Ar is a 3-cyclopentyloxy-4-methoxyphenyl or phenyl group.

10. A compound which is:

(E)-N-[3-(3-Cyclopentyloxy-4-methoxyphenyl)-2-(4-pyridyl)propenoyl]-(1R)-10,2-bornanesultam; or (Z)-N-[3-(3-Cyclopentyloxy-4-methoxyphenyl)-2-(4-pyridyl)propenoyl]-(1R)-10,2-bornanesultam; or (E)-N-[3-(3-Cyclopentyloxy-4-methoxyphenyl)-2-(4-pyridyl)propenoyl]-(1S)-10,2-bornanesultam; or (Z)-N-[3-(3-Cyclopentyloxy-4-methoxyphenyl)-2-(4-pyridyl)propenoyl]-(1,5)-10,2-bornanesultam; or (E)-N-3-Phenyl-2-(4-pyridyl)propenoyl-(1R)-10,2-bornanesultam; or (Z)-N-3-Phenyl-2-(4-pyridyl)propenoyl-(1R)-10,2-bornanesultam; or (E)-N-3-Phenyl-2-(4-pyridyl)propenoyl-(1S)-10,2-bornanesultam; or (Z)-N-3-Phenyl-2-(4-pyridyl)propenoyl-(1S)-10,2-bornanesultam.

11. A compound according to claim 10 which is (E)-N-[3-(3-cyclopentyloxy-4-methoxyphenyl)-2-(4-pyridyl)propenoyl]-(1R)-10,2-bornanesultam.

12. A process for the preparation of an R- or S-isomer of a compound of formula (2):

Ar—CHCH$_2$R$^4$ (2)
$R^3$ wherein each of Ar, $R^3$ and $R^4$ is independently an optionally substituted monocyclic aryl group or an optionally substituted bicyclic aryl group, said aryl groups optionally containing one or more heteroatoms selected from the group consisting of oxygen, sulfur and nitrogen atoms; and the wavy line means that the configuration of —CH($R^3$)— is either the R- or S-configuration, which comprises (a) reacting a compound of formula (1):

Ar—CH=C($R^4$)COAux (1)

wherein Aux is the residue of a chiral R- or S-auxiliary, with an $R^3$-containing organometallic reagent to yield a compound of formula (3):

Ar—CHCH($R^4$)COAux (3)
$R^3$ (b) cleaving the compound of formula (3) with a thiol, in the presence of a base, to yield a thioester of formula (4):

Ar—CHCH($R^4$)COSR (4)
$R^3$ wherein —SR is the residue of a thiol and R is an organic group; and (c) decarbonylating the thioester of formula (4) to yield the R- or S-isomer of formula (2).

13. A process according to claim 12 which additionally comprises the step of salt formation of the R- or S-isomer of formula (2).

14. A process according to claim 12 wherein the isomer of formula (2) is:

(R)-(+)-4-[2-(3-Cyclopentyloxy-4-methoxyphenyl)-2-phenylethyl]pyridine;

(S)-(−)-4-[2-(3-Cyclopentyloxy-4-methoxyphenyl)-2-phenylethyl]pyridine;

(R)-(+)-4-[1-(3-Cyclopentyloxy-4-methoxyphenyl)-2-(4-pyridyl)ethyl]pyridine; or (S)-(−)-4-[1-(3-Cyclopentyloxy-4-methoxyphenyl)-2-(4-pyridyl)ethyl]pyridine.

15. A process according to claim 12 wherein Aux in the compound of formula (1) is N-(1R)-10,2-bornanesultam or N-(1S)-10,2-bornanesultam.

16. A process according to claim 12 wherein the isomer of formula (2) is (R)-(+)-4-[2-(3-Cyclopentyloxy-4-methoxyphenyl)-2-phenylethyl]pyridine and the compound of formula (1) is (E)-N-[3-(3-Cyclopentyloxy-4-methoxyphenyl)-2-(4-pyridyl)propenoyl]-(1R)-10,2-bornanesultam).

* * * * *